US008515576B2

(12) United States Patent
Lipow et al.

(10) Patent No.: US 8,515,576 B2
(45) Date of Patent: *Aug. 20, 2013

(54) SURGICAL ROBOT AND ROBOTIC CONTROLLER

(75) Inventors: Kenneth L. Lipow, Bridgeport, CT (US); Dennis Gregoris, Toronto (CA)

(73) Assignee: MacDonald, Dettwiler and Associates Ltd., Richmond (CA)

(*) Notice: Subject to any disclaimer, the term of this patent is extended or adjusted under 35 U.S.C. 154(b) by 0 days.

This patent is subject to a terminal disclaimer.

(21) Appl. No.: 13/205,524

(22) Filed: Aug. 8, 2011
(Under 37 CFR 1.47)

(65) Prior Publication Data

US 2012/0035764 A1 Feb. 9, 2012

Related U.S. Application Data

(63) Continuation of application No. 11/603,352, filed on Nov. 20, 2006, now Pat. No. 7,996,110, which is a continuation of application No. 10/738,359, filed on Dec. 17, 2003, now abandoned, which is a continuation-in-part of application No. 09/898,871, filed on Jul. 3, 2001, now abandoned, and a continuation-in-part of application No. 10/321,171, filed on Dec. 17, 2002, now Pat. No. 7,198,630.

(51) Int. Cl.
*A61B 18/00* (2006.01)

(52) U.S. Cl.
USPC .......................................... 700/245; 318/574

(58) Field of Classification Search
USPC ................. 700/245, 259, 254, 247–249, 260; 318/568.11, 568.13, 568.16, 573, 574
See application file for complete search history.

(56) References Cited

U.S. PATENT DOCUMENTS

| 4,274,421 A | 6/1981 | Dory et al. |
| 4,418,698 A | 12/1983 | Dory et al. |
| 4,515,017 A | 5/1985 | McConaghy |

(Continued)

FOREIGN PATENT DOCUMENTS

WO  WO-00/28882  5/2000

OTHER PUBLICATIONS

Article: "A Force-Reflecting Teleoperated Hand System for the Study of Tactile Sensing in Precision Manipulation", Robert D. Howe, Proceedings of the 1992 IEEE International Conference on Robotics and Automation, Nice, France, May 1992.

(Continued)

*Primary Examiner* — Dalena Tran
(74) *Attorney, Agent, or Firm* — Perkins Coie LLP

(57) ABSTRACT

The present invention was developed by a neurosurgeon and seeks to mimic the results of primate neurological research which is indicative of a human's actual neurological control structures and logic. Specifically, the motor proprioceptive and tactile neurophysiology functioning of the surgeon's hands and internal hand control system from the muscular level through the intrafusal fiber system of the neural network is considered in creating the robot and method of operation of the present invention. Therefore, the surgery is not slowed down as in the art, because the surgeon is in conscious and subconscious natural agreement and harmonization with the robotically actuated surgical instruments based on neurological mimicking of the surgeon's behavior with the functioning of the robot. Therefore, the robot can enhance the surgeon's humanly limited senses while not introducing disruptive variables to the surgeon's naturally occurring operation of his neurophysiology. This is therefore also a new field, neurophysiological symbiotic robotics.

15 Claims, 20 Drawing Sheets

(56) References Cited

U.S. PATENT DOCUMENTS

| | | | |
|---|---|---|---|
| 4,592,572 | A | 6/1986 | Instance et al. |
| 4,913,155 | A | 4/1990 | Dow et al. |
| 4,933,043 | A | 6/1990 | Instance et al. |
| 5,152,294 | A | 10/1992 | Mochizuki et al. |
| 5,159,931 | A | 11/1992 | Pini et al. |
| 5,174,605 | A | 12/1992 | Instance et al. |
| 5,460,179 | A | 10/1995 | Okunuki et al. |
| 5,487,388 | A | 1/1996 | Rello et al. |
| 5,690,635 | A * | 11/1997 | Matsen et al. .......... 606/88 |
| 5,762,458 | A | 6/1998 | Wang et al. |
| 5,943,914 | A | 8/1999 | Morimoto et al. |
| 6,000,297 | A | 12/1999 | Morimoto et al. |
| 6,096,004 | A | 8/2000 | Meglan et al. |
| 6,104,158 | A | 8/2000 | Jacobus et al. |
| 6,201,984 | B1 | 3/2001 | Funda et al. |
| 6,245,028 | B1 | 6/2001 | Furst et al. |
| 6,416,520 | B1 | 7/2002 | Kynast et al. |
| 6,463,319 | B1 | 10/2002 | Bucholz |
| 6,676,669 | B2 * | 1/2004 | Charles et al. .......... 606/130 |
| 6,788,999 | B2 | 9/2004 | Green |
| 6,836,703 | B2 | 12/2004 | Wang et al. |
| 6,850,817 | B1 | 2/2005 | Green |
| 6,963,792 | B1 | 11/2005 | Green |
| 6,999,852 | B2 | 2/2006 | Green |
| 7,006,895 | B2 | 2/2006 | Green |
| 7,025,064 | B2 | 4/2006 | Wang et al. |
| 7,027,892 | B2 | 4/2006 | Wang et al. |
| 7,074,179 | B2 | 7/2006 | Wang et al. |
| 7,107,124 | B2 | 9/2006 | Green |
| 7,187,438 | B2 | 3/2007 | Hamamatsu et al. |
| 7,198,630 | B2 | 4/2007 | Lipow |
| 7,574,250 | B2 | 8/2009 | Niemeyer |
| 7,806,891 | B2 | 10/2010 | Nowlin |
| 2002/0082498 | A1 | 6/2002 | Wendt et al. |
| 2002/0120188 | A1 | 8/2002 | Brock et al. |
| 2004/0243147 | A1 | 12/2004 | Lipow |
| 2006/0087746 | A1 | 4/2006 | Lipow |
| 2006/0155263 | A1 | 7/2006 | Lipow |

OTHER PUBLICATIONS

Article: "A review of robotics in surgery," B. Davies, Proc Instn Mech Engrs vol. 214 Part H, Oct. 22, 1999.
Article: "A Robot with improved Absolute Positioning Accuracy for CT Guided Stereotactic Brain Surgery," Yik San Kwon, IEEE.
Article: "A Teleoperated Microsurgical Robot and Associated Virtual Environment for Eye Surgery," Ian W. Hunter et al., Presence, vol. 2, No. 4, fall 1993, 265-280, The Massachusetts Institute of Technology.
Article: "An Active Hand-held Instrument for Enhanced Microsurgical Accuracy," Wei Tech Ang et al., Proceedings of the Third International Conference on Medical Image Computing and Computer-Assisted Intervention, Pittsburgh, PA, Oct. 11-14, 2000.
Article: "Anesthesia for Robotic Heart Surgery: An Overview," John M. Murkin, The Heart Surgery Forum #2001-7281, 4(4): 311-314, 2001.
Article: "Application of robotics to stereotactic neurosurgery," Ronald F. Young, Neurosurgical Research, 1987, vol. 9, Jun.
Article: "Comparison of Robotic Versus Human Laparoscopic Camera Control," Louis R. Kavoussi et al., The Journal of Urology, vol. 154, 2134-2136, Dec. 1995.
Article: "Computer-Guided Microsurgery: Surgical Evaluation of a Telerobotic Arm", B. D. Krapohl, et al., Microsurgery, 21:22-29, 2001.
Article: "Current Status and Future Directions in Computer-Enhanced Video- and Robotic-Assisted Coronary Bypass Surgery," W. Douglas Boyd et al., Seminars in Thoracic and Cardiovascular Surgery, vol. 14, No. 1 (Jan. 2002, pp. 101-109).
Article: "Emerging Technologies for Surgery in the 21.sup.st Century," Richard M. Satava, Arch Surg/vol. 134, Nov. 1999.
Article: "Feasibility of Robotic Laparoscopic Surgery: 146 Cases," Guy-Bernard Cadiere et al., World Journal of Surgery, 1467-1477, 2001.

Article: "Intraoperative Instrument Motion Sensing for Microsurgery," Mario Gomez-Blanco et al., Proceedings of the First Joint BMES/EMBS Conference Serving Humanity, Advancing Technology, Oct. 13-16, 1999, Atlanta, GA, USA.
Article: "Is the Robotic Arm a Cost-effective Surgical Tool?" Karen Dunlap et al., Aorn Journal, Aug. 1998, vol. 68, No. 2.
Article: "ISG Viewing Wand System," Neurosurgery, vol. 34, No. 6, Jun. 1994.
Article: "Machining and Accuracy Studies for a Tibial Knee Implant Using a Force-Controlled Robot," Geert Van Ham et al., Computer Aided Surgery, 3:123-133 (1998).
Article: "Motion Feedback as a Navigation Aid in Robot Assisted Neurosurgery," Matthias Wapler et al., Medicine Meets Virtual Reality, IOS Press and Ohmsha, 1998.
Article: "Neurosurgical Suite of the Future III" Garnette R. Sutherland et al., Neuroimaging Clinics of North America, vol. 11, No. 4, Nov. 2001.
Article: "New Dimensions of Neurosurgery in the Realm of High Technology: Possibilities, Practicalities, Realities," Michael L. J. Apuzzo, Neurosurgery, vol. 38, No. 4, Apr. 1996.
Article: "Quantitative virtual reality enhances stereotactic neurosurgery," Patrick Kelly, vol. 80, No. 11, Bulletin of the American College of Surgeons, Nov. 1995.
Article: "Robot for CT-Guided Stereotactic Neurosurgery," H. Fankhauser et al., Proceedings of the XIth Meeting of the World Society for Stereotactic and Functional Neurosurgery, Ixtapa, Mexico, Oct. 11-15, 1993.
Article: "Robot-Assisted Microsurgery: A Feasibility Study in the Rat," Peter D. Le Roux et al., Neurosurgery, vol. 48, No. 3, Mar. 2001.
Article: "Robotic Stabilization that Assists Cardiac Surgery on Beating Hearts," Yoshihiko Nakamura et al., Medicine Meets Virtual Reality 2001.
Article: "Robotic Surgery," D. Stoianovici, URobotics Laboratory, World Journal Urology (2000) 18: 289-295.
Article: "Robotic Three-Dimensional Positioning of a Stimulation Electrode in the Brain," J-L. Hefti ET el., Computer Aided Surgery 3:1-10 (1998).
Article: "Robotically Driven Interventions: A Method of Using CT Fluoroscopy without Radiation Exposure to the Physician," Stephen B. Solomon et al., RSNA, 2002.
Article: "Robots in the Operating Room," Kevin L. Ropp, FDA Consumer/Jul.-Aug. 25, 1993.
Article: "The First Clinical Application of a Hands-On Robotic Knee Surgery System," M. Jakopec et al., Computer Aided Surgery, 6:329-339 (2001).
Article: Ales Bardorfer et al, Melecon 2000—10.sup.th Mediterranean Electrotechnical Conference May 29-31, 2000 Cyprus; "Connecting Haptic Interface with a Robot".
Article: Andrew Bzostek et al.; Submitted for Consideration to MICCAI'99; "Force vs. Deforamtion in soft tissue puncture".
Article: Minyan Shi et al.; Virginia Neurological Institute, Jun. 17, 1997; "Integrated Remote Neurosurgery System".
Article: Rajesh Kumar et al.; "Performance of Robotic Augmentation in Microsurgery-Scale Motions"; John Hopkins University (undated).
Article: Rajesh Kumar et al.; Proceedings of the 2000 IEEE International Conference on Robotics and Automation; "Preliminary Experiments in Cooperative Human/Robot Force Control for Robot Assisted Microsurgical Manipulation".
Article: Russell Taylor et al.; International Journal of Robotics Research, 18 (12): 1201-1210 Dec. 1999; "A Steady-Hand Robotic System for Microsurgical Augmentation".
Article:"NeuRobot: Telecontrolled Micromanipulator System for Minimally Invasive Microneurosurgery—Preliminary Results," Kazuhiro Hongo et al., Neurosurgery, vol. 51, No. 4, Oct. 2002, 985-988.
Articles from: "Current Problems in Surgery," Matthew B. Bloom et al., vol. 39, No. 8, Aug. 2002, Mosby Corporate, pp. 736-739.
Internet Article: "Robotic surgery, telerobotic surgery, telepresence, and telementoring", G.H. Ballantyne, http://link.springer.de/link/service/journals/00464/contents/01/8283/pape-r/body.html, 2002.
Internet Article: http://www.mein.nagoya-u.ac.ip/activity/introduction.html; Cellular Robotic System (CEBOT); Dec. 3, 2002.

The Internet Article: "A Robot that Fixes Hearts," Rob Younge et al., EBSCOhost Full Display, Source U.S. News and World Report, Dec. 25, 2000-Jan. 1, 2001, vol. 129, Issue 25, p. 50.

Web page Cardiothoracic Surgery at the Ohio State University of Nov. 18, 2002; "The DaVinci Robot"; Nov. 18, 2002. cited by other.

Web page http://www.globaltechnoscan.com/21stMar-27thMar01/robot.htm; "Robot-assisted brain surgery is feasible . . . ", Dec. 3, 2002.

Web page http://www.observer.co.uk/uk.sub.--news/story/0,6903,542571.html; "Brain surgery by robot gives hope to Parkinson's sufferers"; Dec. 3, 2002.

Web page http://www.robotbooks.com/robot-surgeon.htm; "Robots in the News"; Dec. 3, 2002.

Web page http://www.time.com/time/health/article/0,8599,128361,00.html; "Forceps! Scalpel! Robot!"; Oct. 18, 2002.

Web page: http://www.bmj.com/cgi/content/full "Robots in operating theatres" Nov. 12, 2000.

Web page: http://www.neurosurgery-online.com/abstracts/4803/NURO48030584.s- ub.--abstx.html; Peter D. Le Roux et al.; Robot-assisted Microsurgery: A Feasibility Study in the Rat; Dec. 3, 2002.

Web page: http://www.sensable.com/haptics/haptics.html; Haptics Research; Dec. 3, 2002.

\* cited by examiner

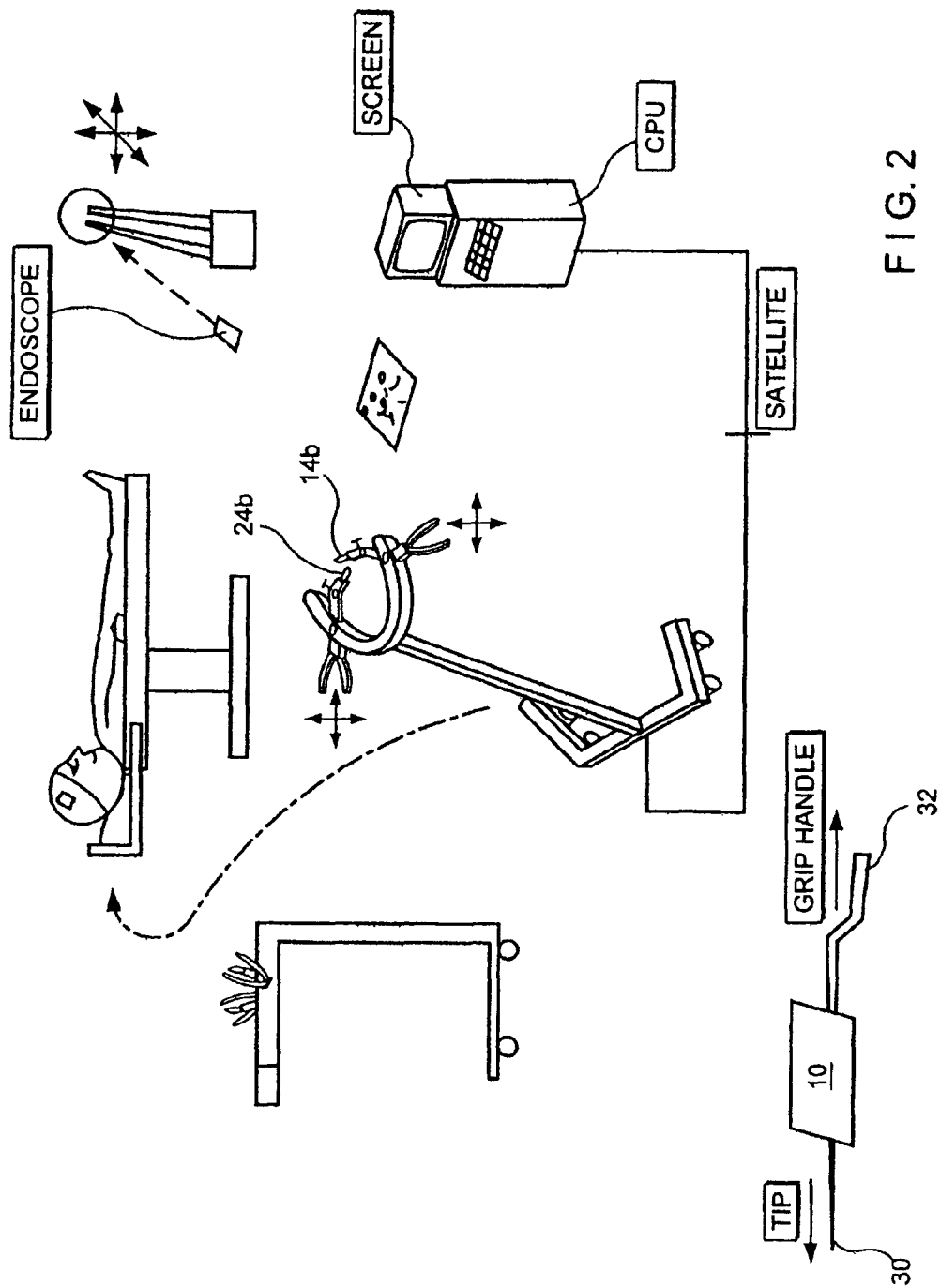
F I G. 2

SURGICAL ROBOT AND ROBOTIC CONTROLLER

The present application is a continuation of U.S. patent application Ser. No. 11/603,352, filed on Nov. 20, 2006, which is a continuation of U.S. patent application Ser. No. 10/738,359, filed Dec. 17, 2003, which is a continuation in part of U.S. patent application Ser. No. 09/898,871, filed Jul. 3, 2001, now abandoned, which is a continuation in part of U.S. patent application Ser. No. 10/321,171, filed Dec. 17, 2002, all of which are incorporated by reference herein in their entireties.

BACKGROUND

The present invention relates to the field of robotic and computer assisted surgery, and more specifically to equipments and methods for robotic and computer assisted microsurgery.

As shown in U.S. Pat. No. 5,943,914 to Morimoto et al., "Master/slave" robots are known in which a surgeon's hand input is converted to a robotic movement. This is particularly useful for motion scaling wherein a larger motion in millimeters or centimeters by the surgeon's input is scaled into a smaller micron movement. Motion scaling has also been applied in cardiac endoscopy, and neurosurgical target acquisition brain biopsy (with a needle) but only in one degree of freedom, for example only for insertion, not for a full range of natural hand movement directions, .e., not for all possible degrees of natural motion, Cartesian, spherical or polar coordinate systems or other coordinate systems.

Further, in the prior art, surgical robots have been purposefully designed to eliminate the natural hand tremor motions of a surgeon's hand which is about a 50 micron tremor which oscillates with some regularity. The common presumption is that tremor motion creates inaccuracies in surgery. Therefore, robots have been tested which entirely eliminate the surgeon's natural hand tremor. See "A Steady-Hand Robotic System for Microsurgical Augmentation" Taylor et al., *International Journal Of Robotics Research*, 18(12):1201-1210 December 199, and also see "Robotic-assisted Microsurgery: A Feasibility Study in the Rat" LeRoux et al., *Neurosurgery*, March 2001, Volume 48, Number 3, page 584

The way the primate body handles proprioceptive perception is via sensory feedback scaling (up and down) at the muscular level through the intrafusal fiber system of the Gamma efferent neural circuit. This system responds dynamically to changes in the anticipated muscle performance requirement at any instance by adjusting muscle tone with increased discharging for arousal and attention focusing states, and decrease output for resting and low attention states. The muscle spindle apparatus that does this is located in the muscle body, therefore feedback sensory scaling for muscle positioning, force, length and acceleration is partly programmed at the effector level in "hardware" of the body, i.e., the muscle itself. The evidence indicates a 10 cycle per second refresh rate for the human neurophysiological system in general.

Joint position and fine motor function of the fingers occurs through unidirectional (50% of fibers) and bi-directional (50% of fibers) sensing at the joint structure. This coding is for rotation about an axis, but not for force and no clear speed of rotation feedback.

Cutaneous receptors in the skin code for motion, by modulating higher centers in the thalamus and cerebral cortex. This can be timed to about 75 ms delays before motion occurs, three neuronal synaptic transmission delays. These sensors are primarily distal to the joint of rotation and distal in the moving effector limb. Finally, the sense of contact is totally discrete from the above motion feedback sensory systems and the neural pathways and integration centers in the deep hemispheres and cerebral cortices function independent of motion to a large degree.

Force reflectance sensing is also known in order to provide tactile or haptic feedback to a surgeon via an interface. See "Connecting Haptic Interface with a Robot" Bardofer et al., Melecon 200—$10^{th}$ Mediterranean Electrotechnical Conference, May 29-31, 2000, Cyprus.

However, in testing, all of these techniques ultimately slow down the actual surgery especially when performed in conjunction with a microscope for viewing the operation. The procedure time is typically increased by two to three times. See Robotic-assisted Microsurgery: A Feasibility Study in the Rat" cited above. It is believed that this affect is related to dissonance between a surgeons expectations and the feedback and motions of a surgical robot in use.

Another major design issue regards the choice between locating the surgeon in his normal operating position adjacent to the surgical field or locating the surgeon more remotely from the normal operating position at a terminal with a joystick and viewing screen for example. The prior art elects to locate the surgeon remotely from the traditional operational position about the head and to use monitors to display the operation to the surgeon.

SUMMARY OF THE INVENTION

The present invention was developed by a neurosurgeon and seeks to utilize the results of primate neurological research which is indicative of a human's actual neurological control structures and logic. Specifically, the proprioceptive and tactile neurophysiology functioning of the surgeon's hands and internal hand control system from the muscular level through the intrafusal fiber system of the neural network is considered in creating the robot and method of operation of the present invention. Therefore, the surgery is not slowed down as in the prior art devices, because the surgeon is in better conscious and subsconscious natural agreement and more accurate harmonization with the robotically actuated surgical instruments based on neurological mimicking of the surgeon's behavior through the functioning of the robot. Therefore, the robot can enhance the surgeon's humanly limited senses while not introducing disruptive variables to the surgeon's naturally occurring operation of his neurophysiology. This is therefore also a new field, neurophysiological symbiotic robotics.

One result of the present invention, and associated discoveries, was that preservation of the hand tremor motion was unexpectedly found to help to maintain a natural and efficient synergy between the human surgeon and the robotics, and thus not disrupt the normal pace of surgery. This is believed to be because the present invention recognizes that the surgeon's own neurophysiology beneficially uses tremor motion, and moreover the neurophysiology of the surgeon expects and anticipates the tremor to exist for calibration purposes. For example, at the muscular level, tremor is used neurologically for automated feedback sensory scaling and also as part of probing, positioning, and training process of the muscle spindle and muscle. Therefore, human muscle actually performs some calibration and "thinking" itself including anticipating forces to come based on historically learned data or instinct. Thus, preservation of hand tremor may be counter-intuitive, and the opposite of what is taught and suggested in the art.

Additionally, the present invention locates the operator interface of the controller robot to work in basically the same orientation and location as in a standard manual operation. In neurosurgery for example, the controller robot may be included in a halo structure fixed to the patient's head in much the same way as a standard retractor system is affixed. Alternatively, the controller robot may be located on a stand, the body, the surgical table or on a rolling or portable platform. In this manner, the surgeon is not immediately forced to operate in an unnatural, detached and isolated environment which is foreign to traditional procedures to which his own body and neurological responses are accustomed.

Therefore, in summary, the present invention in its various controller robot embodiments may include the following features which may be adjustable by the surgeon to his or her individual requirements:

Hand tremor sensing, management, modulation and smoothing with scaling capability;

Motion sensing and scaling;

Force sensing and scaling including squeeze force scaling, and force reflectance feedback scaling;

Contact sensing and indicating;

Contact reflectance sensing, i.e., reflectance force sensing on the tip of an instrument;

Endoscopic "tip vision" sensors located to look down the tip of the surgical instrument;

External source interface capabilities, including but not limited to, magnetic resonance imaging, computer aided tomograph, and continuous frameless navigation;

Microscope interface capabilities; and

Instrument selection interface capabilities to allow automated picking of surgical instruments.

The present invention may be embodied in a controller robot for performing surgical procedures. The controller robot may have a robotics portion. The robotics portion may have at least one surgical instrument. The controller robot may also have an interface portion having a display and an input device. The controller robot may also have a controller portion having hardware and software for transforming input provided by a surgeon operator via the interface portion into motion of the surgical instrument of the robotics portion. The robotics portion may also have force detection sensors for determining force reflectance from tissue in contact with the surgical instrument.

Alternately, the present invention may be embodied in a method of controlling a surgical instrument connected to a surgical robot wherein the first step may be locating a controller robot between a handle and a surgical instrument. Next, incident tremor force components (TF) present on the handle generated by the surgeon's hand may be sensed. Then, an incident motion force (MF) component present on the handle generated by the surgeon's hand natural motion (NM) as the surgeon moves the handle may be sensed. Then, the incident tremor force (MTF) components in the controller robot may be modulated and scaled. Then incident motion force (MMF) components in the controller robot may also be modulated and scaled. Then, a modulated and scaled output movement (MSOM) including the modulated and scaled incident motion force (MMF) and the modulated and scaled incident tremor force (MTF) in the controller robot for moving the surgical instrument via the controller robot, in all degrees of instrument freedom, in response to the natural movement (NM) inputted by the surgeon on the handle, may be created. A modulated and scaled movement (MSOM) to move the surgical instrument with all anatomically possible degrees of human hand motion freedom, in response to a respective natural movement (NM) inputted by the surgeon on the handle may then be outputted to the surgical instrument. Incident reflectance force (RF) components from the surgical instrument in the controller robot when the surgical instrument is near body tissue may then be sensed. The reflectance force (RFMS) components in the controller robot may be modulated and scaled. The modulated and scaled reflectance force (RFMS) may then be imposed on the handle. Furthermore, a contact/non-contact condition may be sensed at the surgical instrument, and provided to the surgeon via a display to the surgeon.

BRIEF DESCRIPTION OF THE FIGURES

FIG. 2 is top view of a second embodiment of the controller robot in which the controller robot is affixed to a stand.

FIG. 3 is a representation of a controller robot in operation with associated data displays to.

FIG. 5b shows a portion of the prior art mount of FIG. 5a.

DETAILED DESCRIPTION OF THE INVENTION

Figure 4:
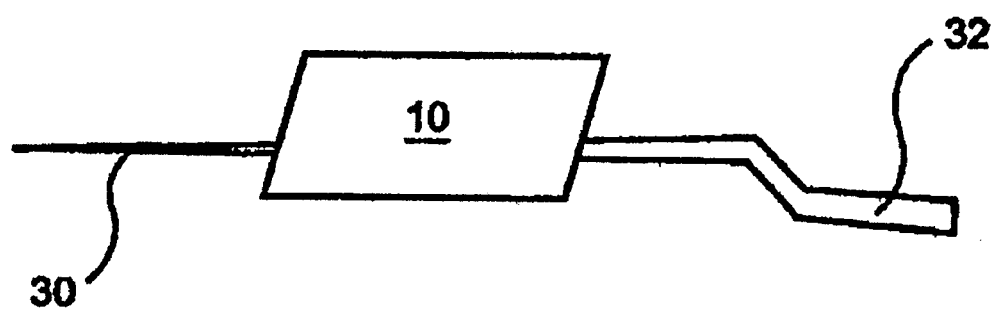
FIG. 4 shows a conceptual representation of an instrumented test.
Figure 5A:
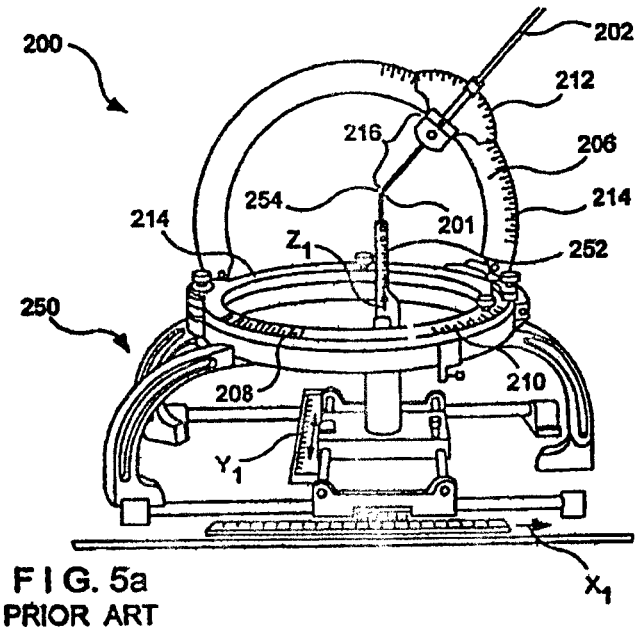
FIG. 5a shows a prior art mount for surgery from U.S. Pat. No. 6,463,319.
Figure 5B:
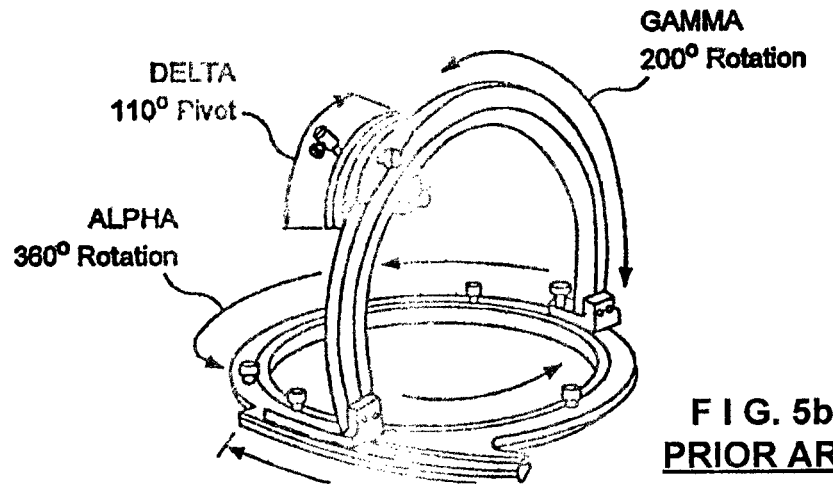

FIG. 4 shows conceptually how the present invention creates a virtual surgical instrument by placing controller robot 10 between the surgical instrument 30 and the handle 32 of the instrument. In this way, the surgeon is not isolated or made remote from the operation, but instead remains in an environment to which he is accustomed. Although the conceptual drawing illustrates a structural connection between the instrument or instrument and the handle, the controller robot may be indirectly linked between the instrument and the handle.

Extrapolating new surgical concepts from known primate research have been critical to method of the present invention, as described generally below.

Figure 1:
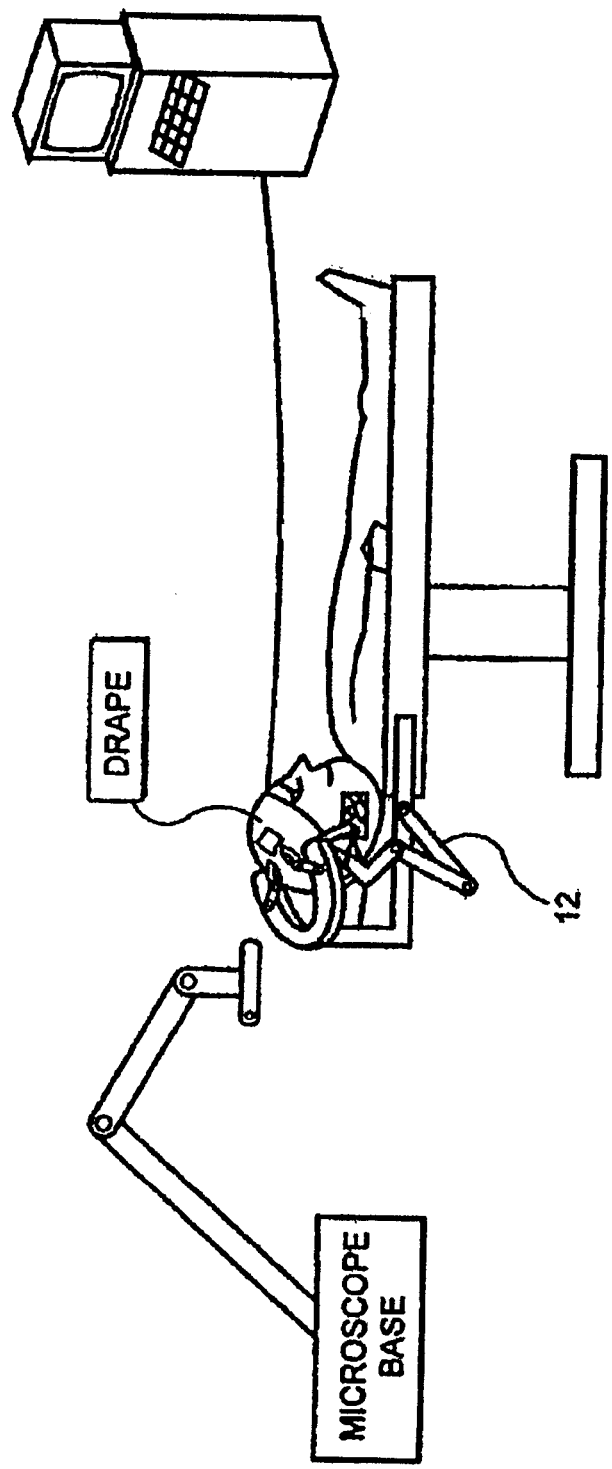
FIG. 1 is a side view of a patient on an operating table with a controller robot engaged to a patient.
Figure 3:
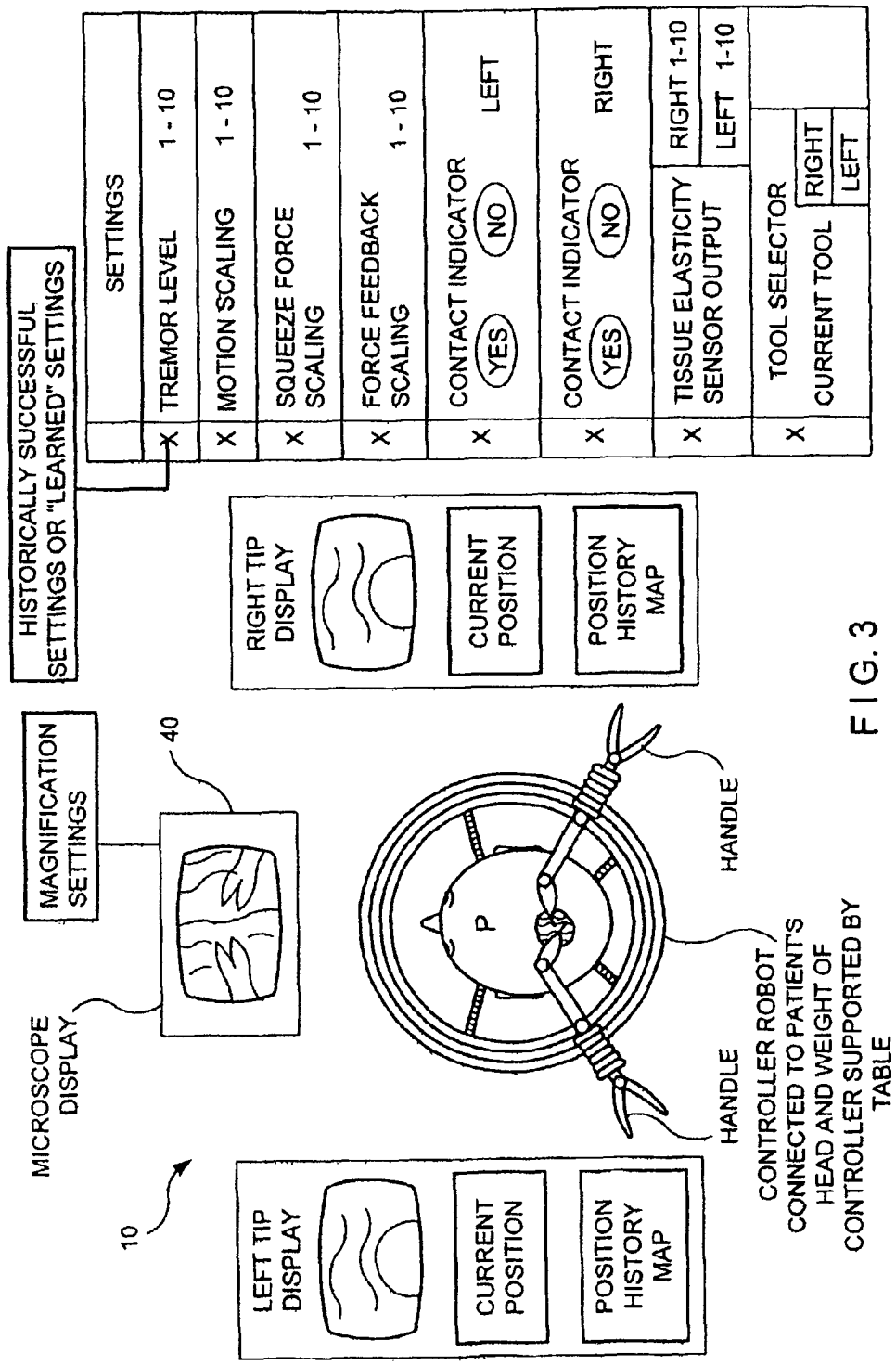

Therefore, as shown in FIGS. 1-3, in the controller robot 10 of the present invention, the creation of the perception of "contact" per se in a surgical robot controller robot 10 should not be based on acceleration/motion reflectance, but rather should be based purely on a binary sense of touch (see "contact indicator" display in FIG. 3) in order to move properly be consistent with the human neurological system; which is different from motion sense.

In a human, the motion sense takes over after contact information has been initiated with a fairly fixed delay measured in milliseconds. In the present invention, limitation of contact information may be transferred through the controller robot 10 to the handle 32 to the surgeon's hand through a physical feedback such as a jerk or vibration, or optically or audibly through a display verifying the contact with the target or proximate tissue in the surgical field.

True force reflectance perception has to have high refresh rates measured in milliseconds. This is consistent with numbers described in the prior art literature which give tactile bandwidths on the order of 500-1000 Hz. For instrument contact with soft surfaces, 100-200 Hz may be more than adequate.

Muscle sensing seeks information regarding amplitude and time with suitable rise and fall curves to allow to synthesize the discrete motor performance function in question virtually in the controller robot.

Also, the fact that the entire human sensory/motor neurophysiologic system works in an "anticipatory mode" with modulation by internal experience and external sensory data indicated above may be utilized in the control function between the operation and the instrument. The human anticipatory mode defines the need for suitable anticipatory delays between contact, muscle loading and neural transmissions times. All of these parameters may be scrutinized subconsciously by the operator via optical feedback (microscope direct vision or endoscopic instrument tip tracking) during the surgery.

Figure 1A:
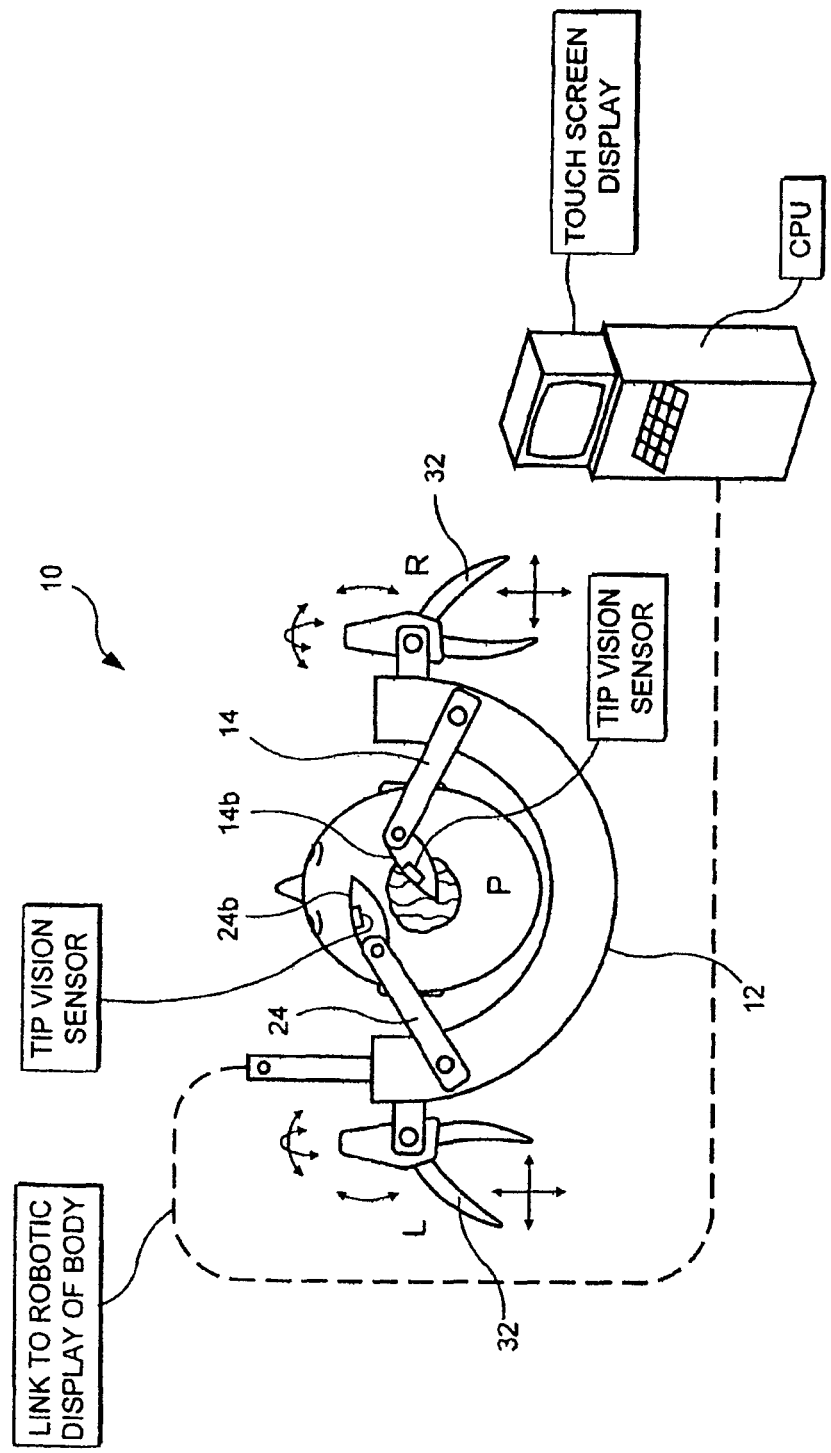
FIG. 1a is a top view of the controller robot engaged to a patient.
Figure 1B:
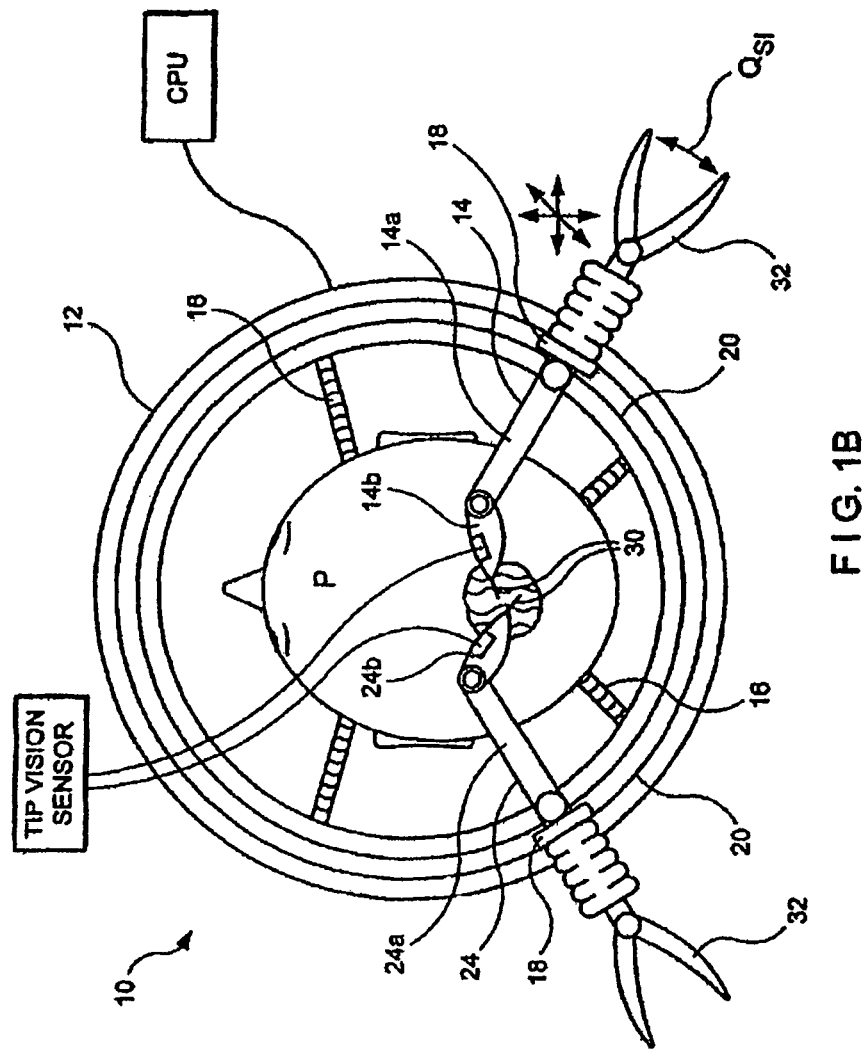
FIG. 1b is a top view of the controller robot engaged to a patient.

In light of the above, a first embodiment for a controller robot 10 is discussed below. FIGS. 1a and 1b show the parts of a controller robot 10 located about a head during surgery. A pinned head holder 12 may be attached via cranial screws 16 to a patient P. The pinned head holder 12 may provide a base for mounting a right robotic arm 14 and a left robotic arm 24 via robotic arm mounts 18. Robotic arm mounts 18 are shown as motorized and may provide for controlled motion including motion on the micron scale or smaller, and may be moveable and stabilized in radial tracks 20. The robotic arms may include sub-arms such as those shown in 14a, 14b, 24a, and 24b. Alternatively, the robot arm may be mounted on a portable tray system which would be fixed to the table which is turn fixed to the patient or other combination for fixation. Surgical instruments may be located at the end of the robotic arms as shown and may be interchangeable. An automated instrument changer such as a carousel is contemplated as well. Handles 32 may mimic actual handles from manual surgical instruments. i.e., they may be the same size and shape, and can be squeezeable or fixed, in order to provide realism to the surgeon.

FIG. 3 shows a number of the data displays which are envisioned as part of controller robot 10.

Typically, a microscope display 40 is used to view a neurosurgical surgical field, such as, for example, a procedure where surgical movements of the surgical instrument tips can be on the order of 100 micrometers. When viewing the visual operation through the microscope the surgeon may be viewing a magnified image so that visual motions of an instrument are magnified. Therefore, motion scaling wherein a controller robot scales down the surgeon's movement of for example to 1 cm to 100 micrometers may be useful.

Therefore, a settings display 50, which may include a motion scaling feature, may be included as part of controller robot 10. The display 50 may include hardware which runs software to control the motorized robotic arms. The display 50 may include a touch screen or other interface, however the software, and hardware may be of any suitable design and this invention is not limited to any particular hardware, software or robotics per se. The present invention prefers to use robust hardware and software platforms for control electronics as required for space based applications where failure prevention is paramount. Applicable ISO and/or IEEE standards may provide further information regarding applicable format tolerances. Each surgeon who uses the robot controller 10 may store his or her personal settings so that his or her personal settings can be restored at a later time, and thus the machine may not have to be retrained.

Returning to FIG. 3, other adjustable settings are shown. An unexpected result of the present invention in concept is the significance of tremor regulation and management including both scaling and smoothing of the tremor oscillation. Hand tremor is a spurious motions which may be present in surgery. Neurological tremor is usually a 50 micrometer (or micron) range excursion and is an oscillation with some regularity that increases with stress. A trained neurosurgeon's hand tremor is usually in the range of 50 to 100 microns, i.e., under a millimeter. The present concept implements the results of primate research which suggests that hand tremor is not an unwanted artifact of evolution, but rather a useful and necessary product of human evolution used for natural calibration. Typically, a hand tremor frequency can be at about 8 cycles per second and this regularity may be used by the surgeon's nervous system to calibrate his movements. The human nervous system uses tremor to calibrate its movements almost automatically or subconsciously, and particularly in conjunction with coordination with optical recognition, i.e., hand/eye coordination, such as when a surgeon moves his hands his eyes register and acknowledge the tremor which is used to calibrate his movements neurologically. This neurological fact is ignored by systems which seek to entirely filter and eliminate neurological tremor. This neurological operation may be utilized by the present invention to provide consistent feedback to a surgeon utilizing the controlled robot. Thus, such utilization may create tremor motion at the tip of the surgical instrument, such that a surgeon looking through a microscope at the tip of his hand held instrument will see tremor motion and his own neurological system within his body will use tremor to neurologically and automatically calibrate his eye motions with his hand motion. Therefore, such tremor management may be important to surgeons and other human mimicking robotics.

In practice, due to magnification under a microscope during microsurgical procedures, the surgeon's own optical system is not in 1:1 natural correspondence with the optical image. Therefore, "tremor scaling," i.e., modification and adjustment of the force of the tremor outputted to the surgical instrument to be harmonized at a natural level with the optical magnification selected, may be a very important concept of the present invention which can be provided via the controller robot 10. Such tremor scaling may help avoid impeding the pace of the operation. The tremor scaling feature is preferably also implemented in conjunction and harmony with motion scaling. For example, reducing natural tremor to half speed may improve the surgeon's movement. This is because the controller robot 10 in toto has enhanced the surgeon's movements.

For example, a typical surgeon's real hand motion or excursion of 5 centimeters with the surgical instrument may contain a 50 micron tremor excursion oscillation, and the motion at the surgical instrument tip (at the actual surgical site) may be scaled down by the controller robot 10 to become a 5 millimeter motion (motion scaling) but may also includes a scaled down tremor motion of 2 microns (or any value the surgeon is personally comfortable with given settings based on trial and error wherein such settings may be stored in the controller robot 10 from one surgery to the next). Thus, the controller robot may effectively maintain in a relative fashion, the effect of the surgeon's hand excursion even under magnification under a surgical microscope, through scaling. Therefore, when a surgeon looks at the surgical instrument through a microscope, what he of she may see is a robotically controlled but natural looking 2 micron tremor excursion (minified from 50 microns) over his 5 millimeter motion (minified from 5 centimeters). This may enhance the surgeon's actual useable natural range and allow him to have enhanced capabilities by first allowing him make his hand motions on a human scale of 5 centimeters and then scaling his motion down to 5 millimeters. Therefore, he or she may move his or her hand accurately in the micron range. Such scaling may be performed by the controller robot 10 in all degrees of freedom associated with a surgical instrument in use, or only with regard to selected degrees of freedom. Second, by incorporating and scaling a tremor motion, the natural calibration of the surgeon's neurological system may be maintained when the surgeon looks through the microscope.

Additionally, given that calibration based on tremor is an important feature for proper motion of the surgeon's hand, the ? may assist a surgeon by eliminating or processing anomalies from the tremor oscillation to allow the surgeon's neurological system to better self-calibrate itself, referred to hereafter as "tremor smoothing" or "tremor shaping." Therefore, if a surgeon is looking at the tip of an instrument, his or her optical feedback which is used for controlling his or her hand can be influenced if anomalies and great irregular deviations in his tremor signal are smoothed to be an oscillation with cyclical regularity. Thus, "tremor smoothing" can actually assist the natural neurological calibration, rather than slowing it down by eliminating tremor as taught in the prior art.

It is envisioned that in the present invention the controller robot 10 when first used may have to be trained, i.e., optimal settings determined on animal tissue, in order for the surgeon's initial settings to be derived. Thereafter, the surgeon, while actually using the controller robot 10 on humans, may also store his or her settings which can be analyzed in real time. A surgeon can store multiple modes, and may "shift gears" during a procedure depending on stored settings. Therefore, enabling personalized surgical robotic symbiosis is another new feature of the present invention, such symbiosis may be enhanced by providing the controller with an ability to predictively apply stored settings which gives the controller robot a layer of artificial intelligence which is designed to mimic the artificial intelligence or natural responses naturally present in the neurological system and for example in the muscle tissue.

Force scaling may be incorporated in the robotic controller in all degrees of motion. For example, a neurosurgeon may be capable of applying 0.01 Newtons of force as his or her minimum force. However, delicate tissue may require a smaller force to be applied to avoid damaging the tissue. Therefore, force scaling may allow a surgeon to scale or minify the actual force presented to the surgical instrument 30. This may be accomplished though the controller robot 10. Conversely, feedback forces may be scaled up or magnified. Significantly, this may enhance the surgeon's natural perception of the tissue's resistance, density, and elasticity.

The present invention may enable force scaling in all instrument degrees of freedom, i.e., the scaling is not limited to one direction as in some prior art cardiac endoscopy robots for example. Therefore, all degrees of freedom of movement may be enabled. For example, the controller robot may move a surgical instrument in seven degrees of freedom, and such forces and displacement magnitudes may be sealed or modulated in each of the seven degrees of freedom.

Force feedback or force reflectance may enable the tip of the surgical instrument to relay through the controller robot 10 the feedback forces to the handle 32. Feedback on the handle 32 may be thought of as a virtual reality representation of the microsurgery environment and the tip. Such force feedback may also be capable of being scaled in a continuous real time fashion. Continuous resistance, elasticity, kickback movements, jerks or other movements may be presented at the handle 32 as they occur at the surgical instrument 30 tip. Significantly, some of these forces may be so small that they need to be scaled up in level to be felt by the surgeon. Therefore, force reflectance may enable the surgeon to actually feel feedback via the handle which he is not naturally capable of feeling, thus enhancing his or her sensing of instrument feedback during a procedure.

Contact sensing may also be enabled in the controller robot. Contact is a binary logic circuit in human neurology, i.e., either there is contact with tissue or not. It is not a time varying function of force as in force reflectance above. Therefore, the controller robot 10 may harmonise the body's natural "binary" contact sensing circuit by implementing a binary contact sensor and display (see FIG. 3, Contact "Yes," "No"). Alternately, a scaled jerk motion may also be presented to the handle 32 to represent contact. Such scaling may enable the surgeon to feel small contacts (i.e., delicate tissue) which would not be naturally felt.

Mini-endoscopic tip-vision capability is also taught and suggested by the present invention to enable a view down the tip of the instrument. Such a tip display or "instrument eye view" may enable vision from angles which are impossible to see through a traditional microscope view finder. Displays for such endoscopes are shown as right endoscopic tip display 60 and left endoscopic tip display 70 in FIG. 3. The displays may be capable of showing many views and magnifications, current position and history display of the course the instrument has traveled during the operation. Playback of actual images, "instant re-play of the operation moves" may also be part of the history capability.

It is also contemplated that the handle 32 may be interchangeable and exchangeable to mimic actual standard surgical handles depending on field specific, surgeon specific, or operation specific conditions. For example, some handles may be squeezable, while some may be different shapes. Such handles may be instrumented accordingly to receive relevant impute from a surgeon.

Figure 6:
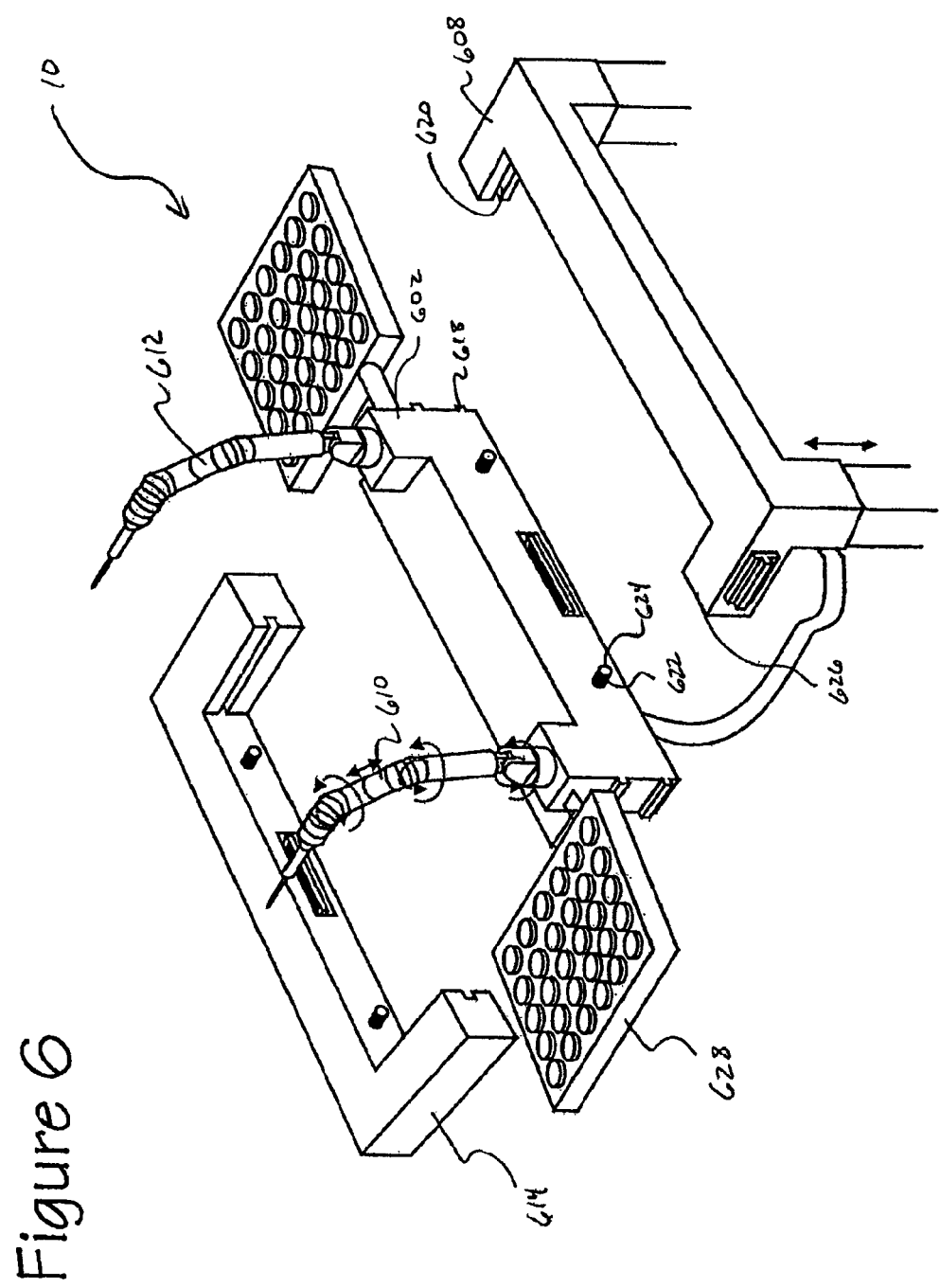
FIG. 6 shows an embodiment of the present invention wherein the controller robot is embodied in controller, robotics, interface, and mobile base portions.

In a second embodiment, the controller robot 10 of the present invention may take the form shown in FIG. 6. The components of the controller robot may include a robotics portion 602, a surgeon workstation portion 604 (not illustrated in FIG. 6), a controller portion 606, and a mobile base 608. The controller portion 606 may be integrated with the robotics portion 602, the workstation portion 604, or the mobile portion 608. The robotics portion 602 may include left and right robotic arms 610, 612 (discussed further below) for carrying out commanded actions. The robotics portion 602 may be adapted to be engaged to an adapter 614 attached to a surgical table 616 (not illustrated in FIG. 6), such that the positioning of the robotics portion 602 relative to the surgical table 616 may be adapted for Various types of procedures on varying portions of a patients anatomy simple by adjusting the position of the adapter 614.

The ability to locate the robotics portion 602 at various locations relative to the surgical table 616 may allow different types of surgery to be accomplished with the same controller robot 10. Furthermore, since an adapter 614 may be moved between surgical tables, use of a controller robot 10 may not be limited to a single operating room. Accordingly, the utility of the controller robot may be maximized, as the need to procure multiple controller robots for multiple operating rooms can be avoided. Finally, an additional efficiency may be gained through the reduction in cross training required by a surgeon where a single piece of equipment is able to replace several different pieces.

The mobile base 608 may allow the components of the controller robot 10 to be portably located within the operating environment as desired. As preparation of a patient may require the fullest access possible to the patient, it may be desirable to minimize the equipment immediately adjacent to the patient during a preparatory phase, while retaining the ability to utilize robotics during the actual procedure. Accordingly, the ability to move at least the robotics portion 602 of the controller robot 10 into and out of the surgical field may provide benefits during the complete surgical procedure.

As shown in FIG. 6, the robotics portion 602 may be provided with features for alternately engaging the robotics portion 602 to a mobile base 608 or to table adapter 614. The engagement between the robotics portion 602 and the mobile base 608 may be accomplished by a tongue in groove joint 616, utilizing a rail feature 618 on the robotics portion 602 and a channel 620 on the mobile base, to form a self aligning and supporting engagement between the robotics portion 602 and the mobile base 608 when the robotics portion 602 is engaged to the mobile base 608. Additionally, retention features 622 such as a threaded retaining pin 624 may be provided to ensure retention of the robotics portion 602 to the mobile base 608 when the robotics portion 602 is engaged to the mobile base 608.

Similar engagement and retention features may be provided between the robotics portion 602 and the table adapter 614. The use of the rail in channel structure assists in orienting and positioning the robotics portion relative to the table adapter 614, such that indexing the position of the adapter 614 to the surgical table may allow correct indexing of the robotics portion 602 to the table 616. With regard to some neurosurgical procedures (as well as other procedures), the patient may be fixed relative to the table 616, such as through the use of positioning screws (such positioning screws are known and used in the neurosurgical art), such that the position of the patient may be indexed to the table 616. Thus, the position of the patient relative to the robotics portion 602 of the controller robot 10 may be established by the indexing of the patient and the robotics portion 602 of the controller robot to the surgical table 616.

Figure 7:
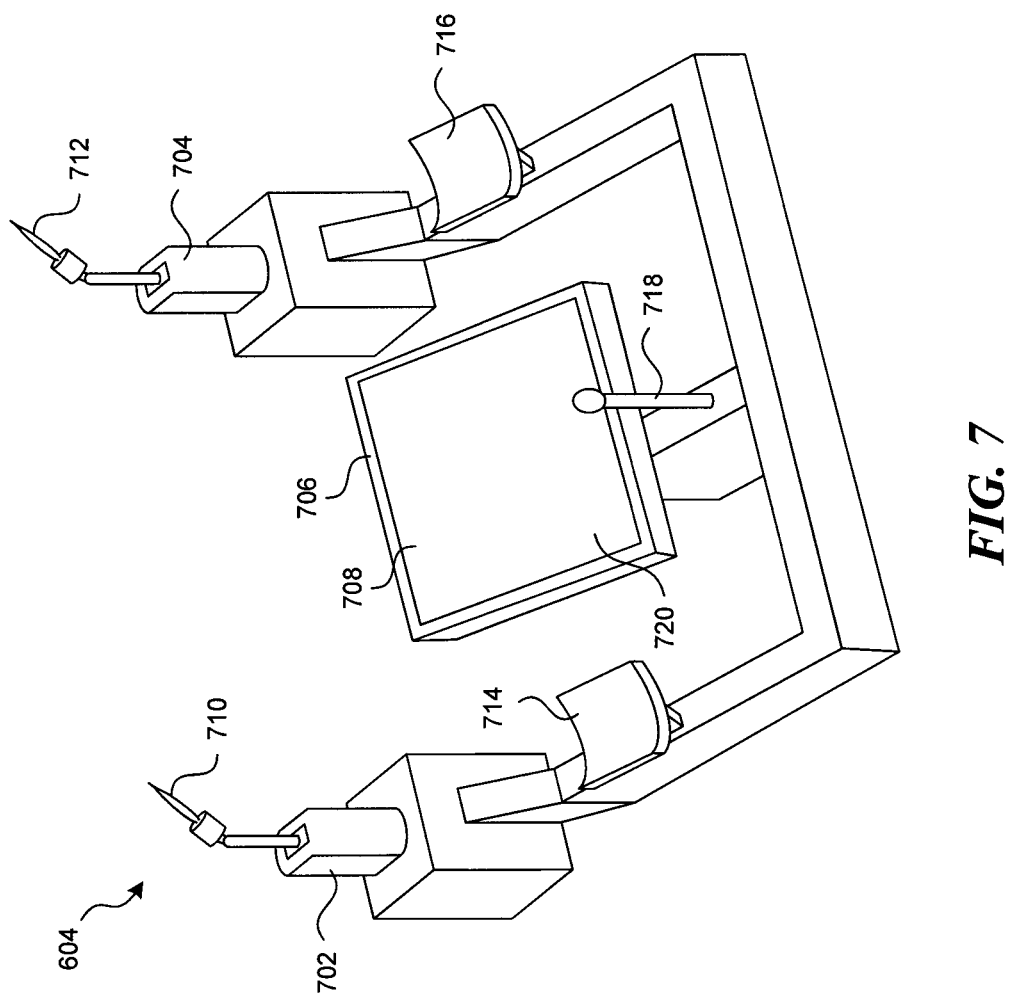
FIG. 7 shows an embodiment of an augmented microsurgical interface.

Dis-engagement of the workstation portion 604 shown in FIG. 7 during procedure, through which a user controls the robotics portion 602, from the robotics portion isolates any potential spurious motions of the surgeon operator from the robotics portion 602, such that such motions are not inadvertently transferred to a patient through an instrument or effector. Such isolation reduces the likelihood of harm as a result of any such spurious motion. Such isolation further may prevent spurious motions of a patient from being transmitted to a surgeon operator during a procedure, thus further reducing the likelihood of harm resultant from spurious motions.

The mobile base 608 may be provided with features for allowing the mobile base 608 to be alternately rolled around within a surgical environment, or fixed relative to a specific position within the operating environment. Such alternating function may be accomplished by providing the mobile base 608 with both rollers 802 (shown in FIG. 8) or casters, as well as jack screws 804 (shown in FIG. 8) to support the mobile base 608 off of the rollers 802 or casters when it is desired that the mobile base 608 not move. Additionally, the robotics portion dock 626 on the mobile base 608 may be height adjustable relative to a floor on which the mobile base 608 is resting, such that the position of the robotics portion dock 626 may be adjusted relative to the robotics portion 602 to allow alignment of the robotics portion 602 relative to the dock 626 to allow engagement of the robotics portion 602 to the dock 626.

The mobile base 608 may also be adapted to have the elements which comprise the surgical workstation portion engageable to the mobile base 608. As shown in FIG. 7, the surgical workstation portion 604 may include left and right controllers 702 704, as well as a user interface 706 for displaying operation parameters and feedback signals to a surgeon using the controller robot 10. The user interface 706 may be a touch-sensitive display, allowing a user to select and set parameters, as well as to view graphic representations of feedback, such as discussed further below. The controller portion 606, which may include software and hardware for converting inputs from the workstation portion 604 into motions by the left and right arms 610, 612, may be integrated into the workstation portion 604, such that the entire controller robot 10, including the robotics, workstation and controller portions 602, 604 and 606 may be transportable as a unit when engaged to the mobile base 608. Alternately, the controller portion may be a preparation unit, attachable to the mobile base, or be remotely located away from the operating environment.

The robotics portion 602 may include two arms 610, 612 having several degrees of freedom to allow correct positioning and orientation of instruments and/or effectors attached to the ends of the arms. The arms may include two sections, having at least two degrees of freedom at each joint, or may have more than two sections allowing movements to be accomplished by lesser motions at each joint.

Figure 9:
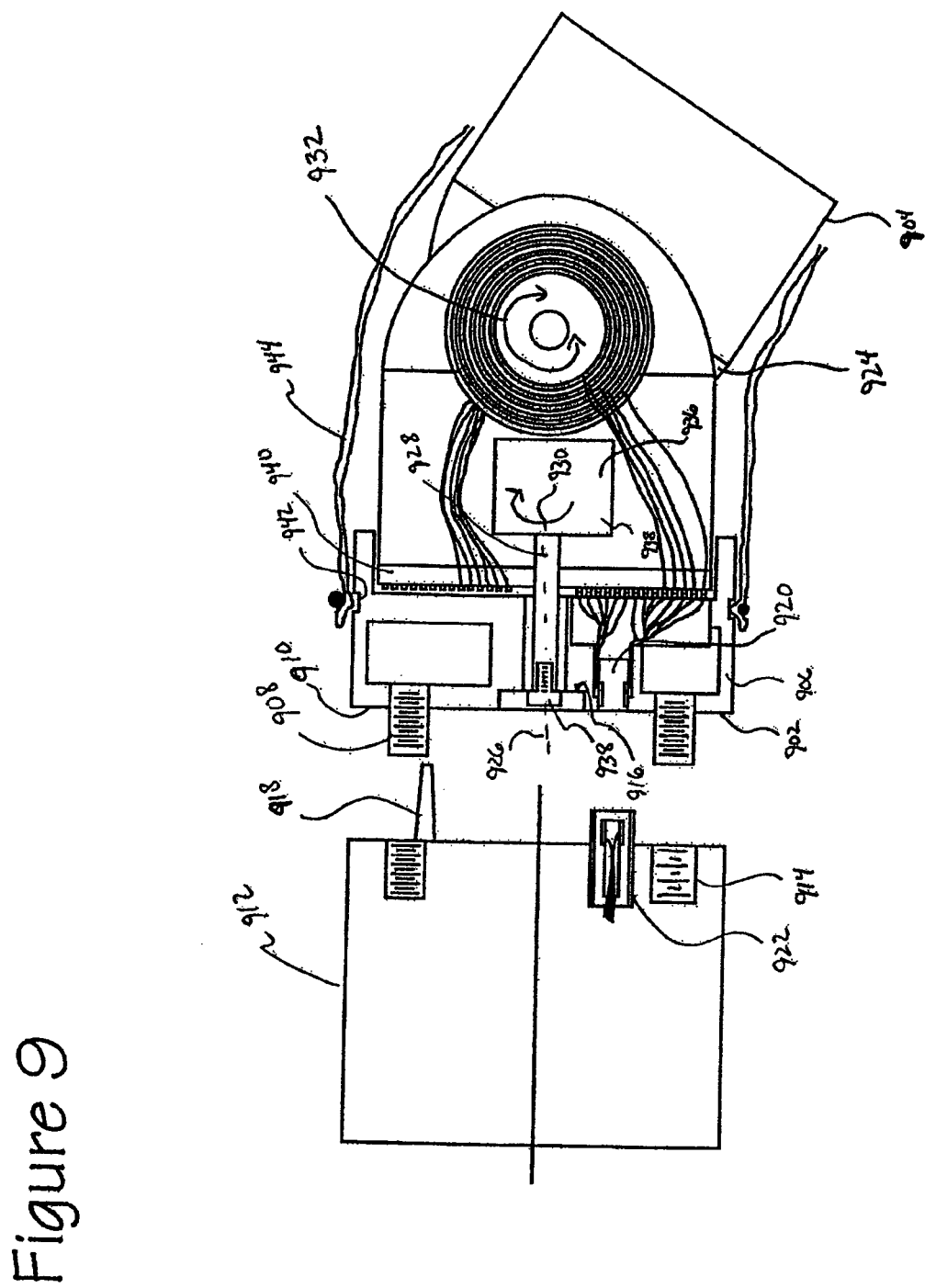
FIG. 9 shows an interface between a robotic arm for a controller robot with a surgical instrument unit.

The ends of the arms 610, 612 may be designed to allow different instruments or instrument magazines to be interchangeably attached to the ends of the arms 610, 612. As shown in FIG. 9, the end 902 of an arm 904 (a non-left/right specification is shown) may be formed by a interchange block 906 having features for engaging a instrument unit, such as those discussed further below. The interchange block 906 may also be provided with instrument retention features, such as threaded rods 908 extending from a face 910 of the interchange block 906, which are adapted to be received by a an instrument unit or instrument magazine (shown generically as 912 or FIG. 9). The threaded rods 908 may be reversibly driven to allow the rods 908 to be alternately threaded into or withdrawn from threaded receiver holes 914 on an instrument unit 912. The interchange block 906 may also be provided with alignment receptacles 916 for receiving alignment pins 918 on the instrument unit 912, to assure proper orientation and positioning of the instrument unit 912 relative to the interchange block 906. A communications receptacle 920 may also be provided on the face of the interchange block 906, for receiving a communications connector 922 on an instrument unit 912 to allow communication of electrical signals between the interchange block 906 and the instrument unit 912.

The interchange block 906 may have two degrees of freedom relative to the wrist 924 of the arm. These degrees of freedom may be a rotational degree of freedom 930 about a finger pin axis 926 extending through a finger pin 928, and a rotational degree of freedom 932 about an axis 934 perpendicular to the axis 926 through the interchange block 906 and an engaged instrument unit. The degree of freedom 930 about the finger pin axis 926 may be provided by mounting the interchange block 906 to a wrist block 936 through the finger pin 928. The finger pin may be provided with a non-circular cross section, such that the interchange block 906 can not rotate about the pin 928. The pin 928 may extend from a wrist motor 938 mounted to the wrist block 936, such that rotation of the pin 928 caused by the wrist motor 938 will cause the interchange block 906 to rotate about that axis 926. The interchange block 906 may be retained to the finger pin 928 by a fastener 939 threaded into the end of the finger pin 928 to retain the interchange block 906 to the finger pin 928. Slip rings 940 may be provided between the interchange block 906 and the wrist block 936 to allow communication of electrical signals between the interchange block 906 and the wrist block 936 during rotation of the finger pin 928. Alternately, a flexible wire bundle (not shown) may be provided between the wrist block 936 and the interchange block 906, although the use of a flexible cable bundle may require imposition of a limit on the range of rotation through which the interchange block 906 may be rotated.

Figure 10:
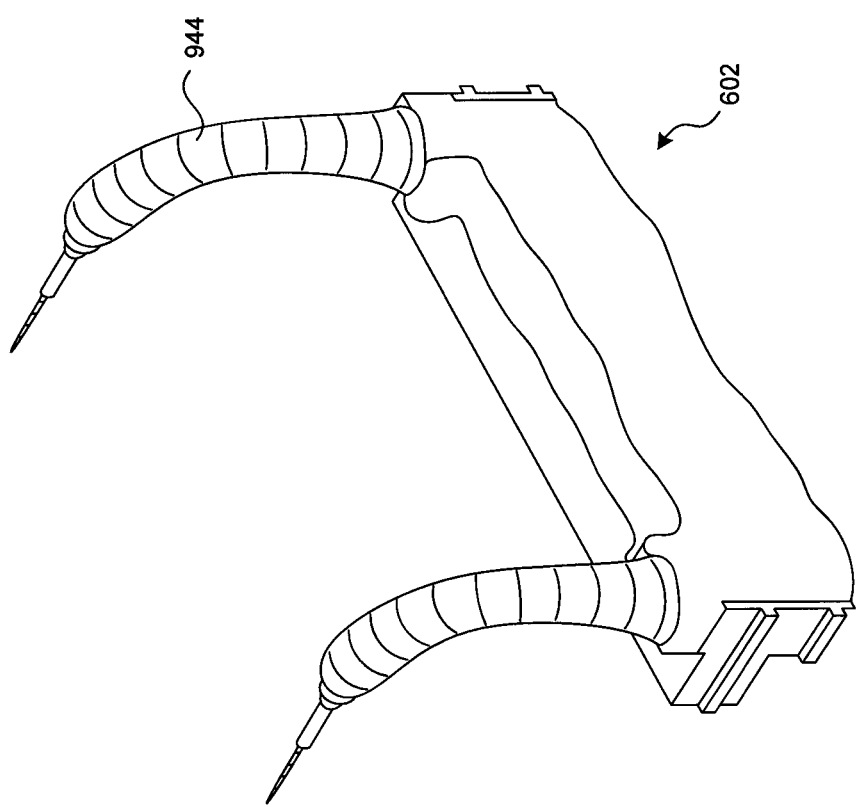
FIG. 10 shows a robotics portion according to present invention over which a sheath has been draped to provide a sterile barrier between the robotics portion and a patient.

The interchange block 906 may be provided with an annular channel 942 surrounding the outer surface 944 of the interchange block 906, to allow a sterile sheath 944 to be retained to the interchange block 906. As shown in FIG. 10, the sterile sheath may extend from the interchange block 906 down the arm to which the interchange block 906 is connected, and may further extend to encompass all or substantially all of the robotics portion 602 to provide a sterile barrier between the robotics portion 602 and a patient on whom the controller robot 10 is being used.

The use of the interchange block 906 allows varied instruments to be implemented on the end of the arm 610, 612, such that the same robotics portion 602 may be used for different surgical procedures simply by changing the available instruments for the arm. Furthermore, the instruments available for use during a procedure may be expanded through provision of instrument units which carry multiple instruments (hereafter referred to as instrument magazines), through the use of instrument trays attached to the robotics portion 602 (such as those shown in FIG. 6 as reference 628), or through the use of instrument trays containing instrument magazines. The incorporation of features which allow an arm 610, 612 to connect to or disconnect from instrument units allows such instrument units to swapped onto the end of the arm 610, 612 with minimal manual intervention from a surgeon operator.

The capability of using multiple instrument units on the arms 610, 612 of the robotics portion 602 requires the adoption of a standard interface between the instrument unit and the interchange block 602. The standard interface should include both the mechanical interface definition, as well as the electrical interface definition. The electrical interface definition should be able to provide available communications paths for each type of signal which may be needed to be communicated between a an instrument unit and the controller portion 606.

Figure 11:
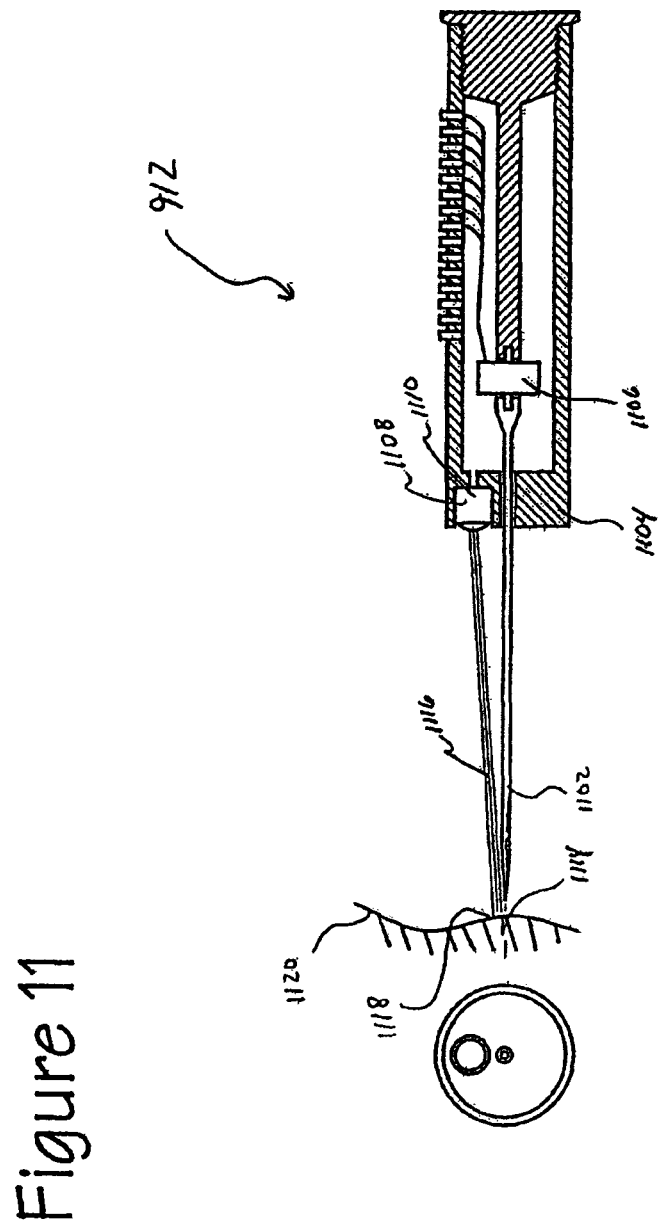
FIG. 11 shows a notional instrument unit as may be used in a controller robot.

An illustrative probe instrument unit is shown in FIG. 11 The probe 1102 shown may be used to press on or move tissue during a procedure. As shown, the probe 1102 may be connected to its instrument unit 1104 through a load cell 1106, which may be capable of measuring forces in one or more directions. The use of the load cell 1106 allows communication of the amount of force that the probe 1102 is applying to be communicated to the controller portion 606, which may then use the information for other purposes, such as for generation of feedback to a surgeon operating the controller robot. The load cell 1106 will likely require the presence of an excitation voltage, as well as available paths for communicating response values from the load cell 1106. These signals may be communicated to the controller portion 606 in either analog or digital form. If the signals are communicated in an analog form, the analog signal would need to be converted to a digital signal in the controller portion 606. Such analog to digital capture capabilities are available in programmable form, such that the same analog to digital unit or units in the controller portion would be able to receive and transform signals from varying types of sensors provided in a instrument unit.

The instrument unit may additionally be provided with features for assisting a surgeon operator in determining the distance of an instrument from a piece of tissue. Although the use of binocular viewing devices can provide depth information, the use of monocular viewers, or two dimensional displays, reduces the availability of visual depth perception cues. Accordingly, it may be desirable to provide cueing for the surgeon operator to assist the surgeon operator in determining distance from and predicting contact with tissue.

One potential visual aid is the addition of a visible light pointer 1108 to indicate the direction in which the probe 1102 is pointing. The power of the light source 1110 must be maintained at a minimum to limit any adverse tissue heating affects. Accordingly, the size of the light source 1110 may be maintained small enough such that the source 1110 may be built into the instrument unit 912, slightly off axis from the probe 1102 itself The inability to have the light 1112 point directly down the axis 1114 of the instrument may be offset by aiming the light 1116 at a point of contact 1118 immediately in front of the position where the probe 1102 would contact tissue 1120, such that that the surgeon would be able to estimate distance to instrument contact based on the gap between the probe 1102 and the projected point of light, relative to the size of the probe 1102 and the viewed motion of the probe 1102.

Figure 12:
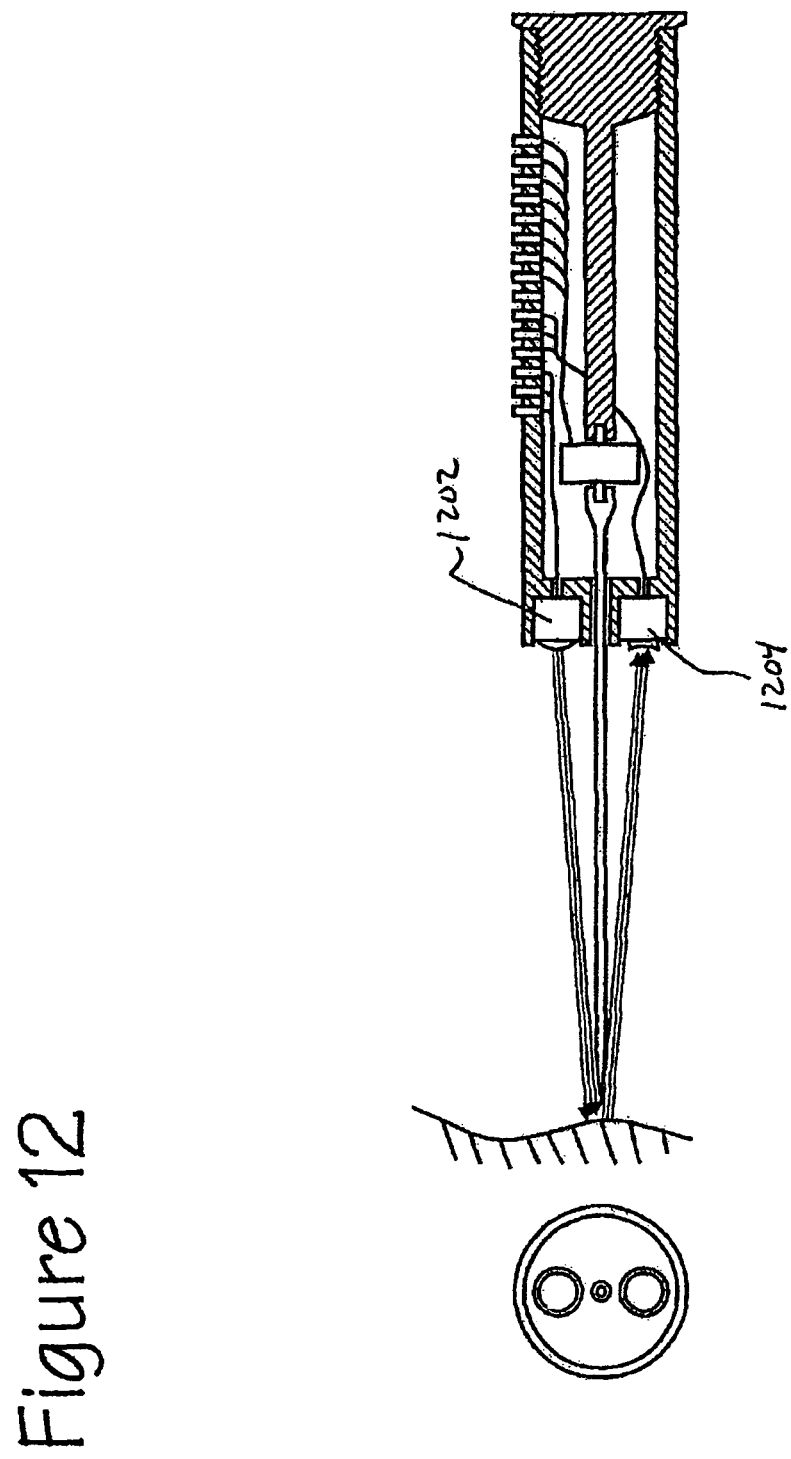
FIG. 12 shows a notional instrument unit as may be used in a controller robot, incorporating distance sensing equipment to provide distance feedback to a surgeon operator.

A variation on the single light distance cueing is the use of a proximity sensor. A proximity sensor may use a transmitter and receiver pair to determine the distance between the transmitter and a surface. The measured distance may be compared to the known length of a probe to determine the distance between the end of the probe and tissue in front of the probe. As shown in FIG. 12, the transmitter 1202 and receiver 1204 may be off-set on opposite sides of the probe 1102, such that the distance being measured is the distance between the end of the probe and the tissue, rather than the tissue off-set a distance from the probe 1102.

The distance between the end of the probe 1102 and the tissue may be represented to the surgeon through a visual or audible display presented on the workstation portion 604. For example, an aural indicator, declining in magnitude until zero at contact, may be provided. Alternately, a graphical read out of the distance between the tissue and the end of the instrument may be presented, or the distance may be presented in a graphical format, such as a vertical bar graph indicating the distance between the end of the instrument and the tissue.

Figure 13:
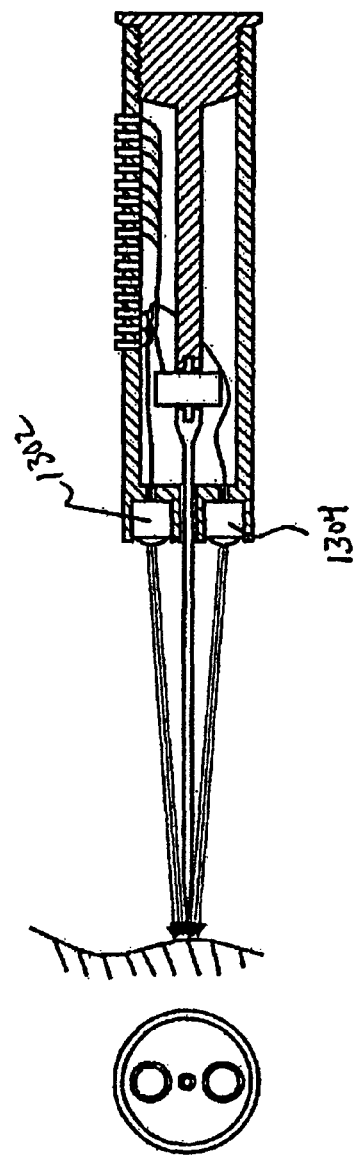
FIG. 13 shows a notional instrument unit as may be used in a controller robot, incorporating dual light pointers to allow the distance between illuminated points to provide distance cueing to a surgeon operator.
Figure 14:
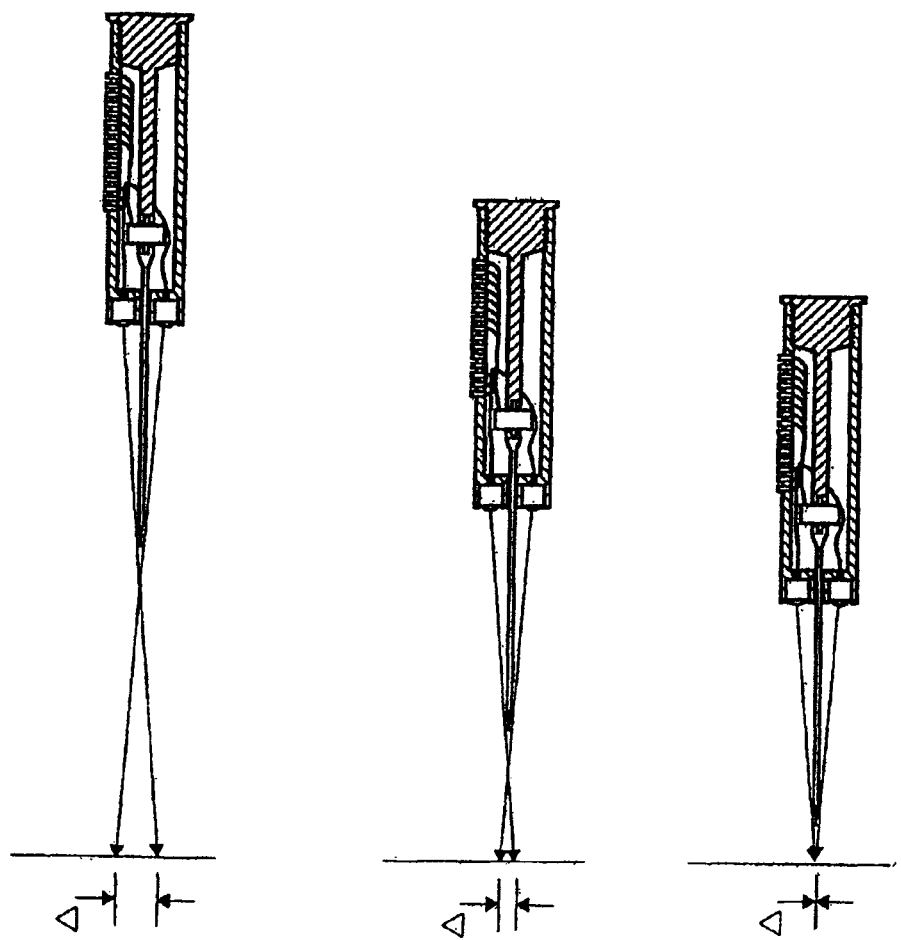
FIG. 14 shows distance differences based on instrument distance for an instrument unit such as that shown in FIG. 13.

As shown in FIGS. 13 and 14, an alternate distance cueing capability may be created by providing two light pointers 1302, 1304, such that when aligned, the points are projected onto the tissue past the instrument. Due to the angle between the light paths, the distance Δ, shown in FIG. 14, between the projected points will increase when the instrument is farther away from the tissue, and decrease as the instrument comes closer to the tissue, until the projected points of light are projected onto the same point immediately before contact.

Figure 15:
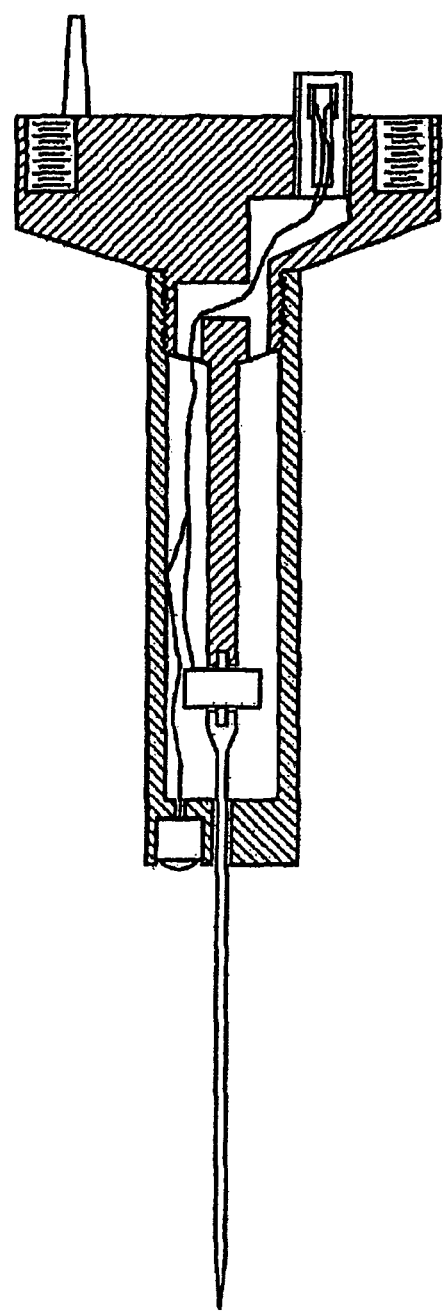
FIG. 15 shows a notional single instrument unit embodying an interface compatible with the interface as shown in FIG. 9.

The instrument units themselves may be provided with the necessary structure for interfacing with the interchange block directly, such as shown in FIG. 15. The instrument unit 912 shown in FIG. 15 is also provided with a video camera 1502 to allow a instrument's eye view to be obtained for the surgeon, such that the view may be provided to a surgeon operator through instrument view displays (such as those shown in FIG. 16).

Instrument units 912 may alternately be designed to allow several instrument units to be contained in a magazine which can be engaged to the interchange block. In such a configuration, some form of ability to extend and retract the individual instrument units must be provided, to allow the motion of the instrument in the operation site without increasing the risk of accidental contact between not-in-use instruments and patient tissue.

Figure 17:
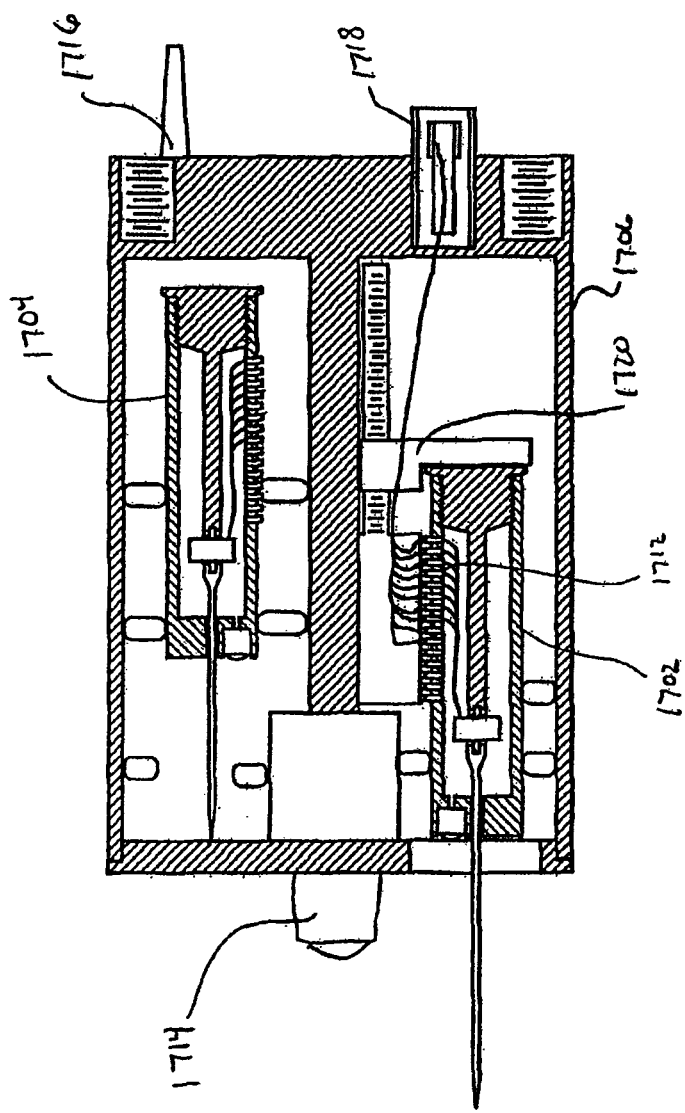
FIG. 17 shows a notional rotary magazine for instruments for a controller robot.

A notional instrument magazine is shown in FIG. 17 showing two instrument units 1702, 1704 in a magazine 1706, with a probe instrument unit 1702 shown in an extended position and a forceps instrument unit 1704 shown in a retracted position. A latch 1708 may be provided to positively engage an extended instrument unit with a drive 1710 for extending the instrument unit. Additionally, contacts 1712 for electrical communication between the instrument unit 1702 and the magazine 1706 may be provided on the outer surface of the instrument unit 1702, such that different instrument units may be engaged in the magazine 1706. Where a magazine 1706 is utilized, a instrument's eye view camera 1714 may be incorporated into the magazine 1706, allowing the complexity of instrument units to be kept at a minimum. The magazine 1706 may be provided with features for engaging the interchange block, including alignment pins 1716, and an electrical connector 1718 for providing a communications path between the instrument units and a remotely located controller portion 606.

The notional magazine shown may use a rotary pattern, in which instrument units are rotated about the long axis of the magazine 1706 until located in a deployment station. In the deployment station, an extension drive 1720 may move the instrument unit forward to a deployed position, in which a surgeon can direct the effector portion of the instrument as required for an on-going procedure.

The use of instrument magazines allows quicker instrument access over requiring a robotic arm to move to a instrument change station, thus providing a more efficient surgical procedure. The selection of instruments to incorporate in a magazine, however, is a trade-off between the allowable size of the magazine, especially in the surgical site, versus the speed with which instruments must be accessible. The use of instrument trays to hold spare magazines with different instrument mixes allows utilization of a magazine tailored for a specific portion of a procedure, while retaining a larger selection such as can be made available on a instrument tray. Thus, the instruments provided in a magazine can be instruments which will be needed rapidly or frequently, while instruments kept in magazines on the instrument tray may be instruments needed at a later point in the procedure, or instruments for which the change-overtime required to change a magazine is not as critical. Furthermore, the instrument tray may be used to hold both instrument magazines and instrument units adapted to engage the interchange block.

Furthermore, the instrument trays may be replaced during a procedure, such that several different mixes of magazines and individual instrument units may be utilized during a procedure. The mixes selected may be dependant on the surgeon utilizing the controller robot, as well as on the procedure being performed. Individual instrument trays may be marked to allow the controller robot 10 to identify instrument magazines and instrument units loaded into a tray, such that the controller portion 606 may display correct selection parameters to a surgeon during a procedure, as well as provide feedback when a instrument is not available in a given mix of instrument units in magazines and individual instrument units. The marking may be accomplished by providing an identifier for a tray, and having a stores list for the tray pre-stored in the controller portion, or may utilize auto-detection capabilities to query instrument units in the tray to identify themselves.

As shown in FIG. 7 the workstation comprises the interface between the surgeon and the controller portion 606, and accordingly should be configured to provide necessary information to a surgeon during a procedure, as well as to receive necessary input from the surgeon during the procedure. Typically, surgeons use vocal commands to receive assistance from other personnel in the operating theater in order to minimize the actions required from the surgeon apart from the procedure itself. For example, a surgeon desiring a different instrument than the one presently in hand may verbally request to be provided with a different instrument. Thus, the workstation may preferably include speech recognition capabilities to allow the surgeon to function in a manner consistent with traditional practices.

Figure 18:
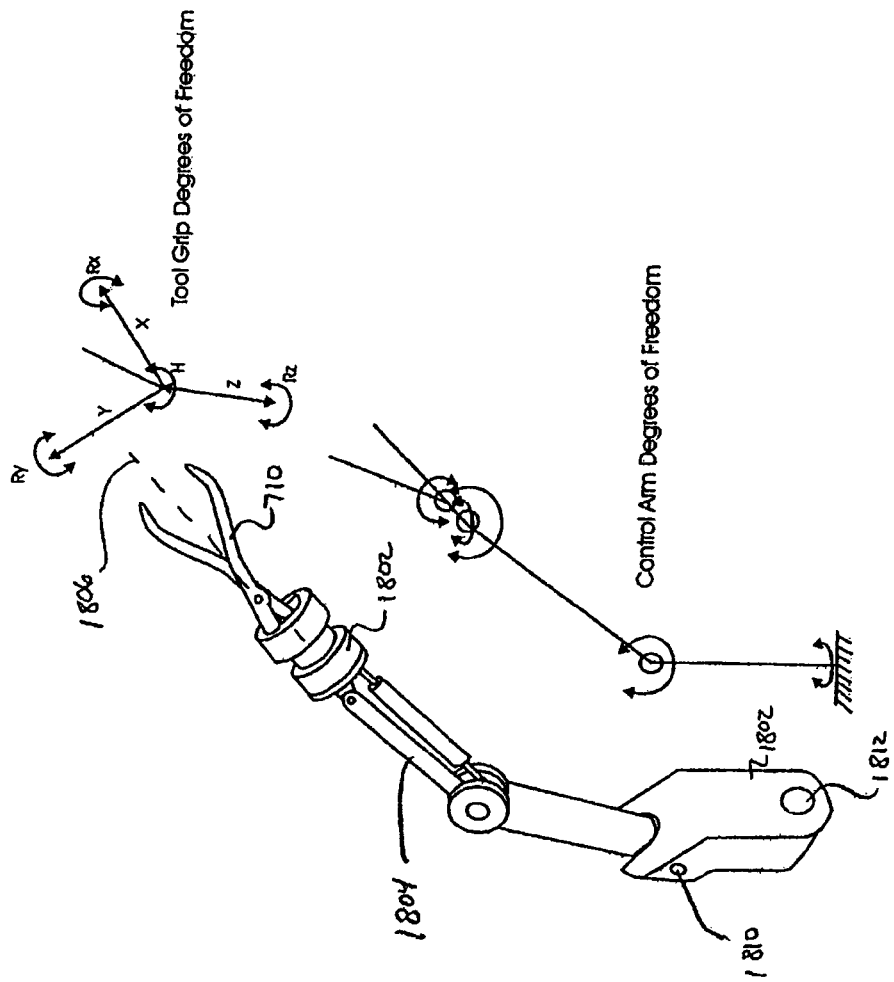
FIG. 18 shows a notional input device for a controller robot.

The workstation may include three types of input capabilities: instrument position, speech recognition, and manual selection. The instrument position input may be received via left and right instrument input devices 702, 704, as described above. The instrument input devices may comprise articulated arms which allow a surgeon to operate handles 710, 712 in a manner consistent with the motions that would be required to manually utilize the instrument in question. As shown in FIG. 18, the handles 710, 712 may be connected to the arms 702, 704 through a load sensing device 1802, able to determine the forces which are being applied to a handle 710. The load sensing device may be a six-axis load cell, able to measure forces in three axes and torques in three axes.

Gross motion of the handle may be allowed through the use of an intermediate arm section 1804 or sections. The intermediate arm section 1804 or sections may utilize one or more degree of freedom motion at each end of the section, similar to the joints of the robotics portion arms, to allow motion to be imparted through the controller. Feedback may be provided to the surgeon through coupling of feedback mechanisms 1808 in each degree of freedom. The handle 710 may be provided with a rotational degree of freedom about the long axis of the handle 1806. A feedback mechanism, such as a stepper motor controlled by the controller portion of the controller robot (not shown), may be used to both provide resistance to rotation of the handle by the surgeon, as well as vary the resistance and reflective force based on feedback being measured at an instrument.

The intermediate arm 1808 or arms may be connected to a base arm 1802 through a joint having one or more degrees of freedom, with each degree of freedom being coupled with a feedback mechanism. Finally, the base arm 1802 may be connected to the workstation structure (not visible in view) through a joint 1812 having one or more degrees of freedom, with each degree of freedom being coupled with a feedback mechanism. Furthermore, each joint should be provided with position sensing means, such a variable resistance potentiometer, to allow the controller portion to determine the position and orientation of the handle while in use.

The mechanism may be designed so as to allow smooth motion in the six degrees of freedom 1814 of a simple handle. The six degrees of freedom may correspond to deflections in three axes, as well as rotation in three axes.

The handle itself may include an additional degree of freedom 1816, such that seven degrees of freedom define motions of the handle. The seventh degree of freedom may be associated with the clamping of the grip, such as where two grips 1818, 1820 are levered to allow an operator to emulate the motion of scissors, forceps, or a hemostat. Since different instruments may require different motions at the handle, the handle may be rapidly interchangeable through the use of a connector 1822 between the handle 710 and the intermediate arm 1808.

Returning to FIG. 7, the workstation structure may additionally be provided with adjustable supports 714, 716 to provide stability to a surgeons arms during a procedure. The ability to adjust the position of the supports 714, 716 allows the surgeon to correctly position his or her arms relative to the handles 710, 712 during a procedure.

Verbal input may be received into the workstation through the incorporation of a microphone 718. The microphone 718 may be external to the structure of the workstation, such as in the form of a clip on microphone or boom microphone extending from the workstation, or may be built internally in the workstation. Such a design choice is dependant on the ability of the microphone 718 selected to adequately detect commends uttered by the surgeon during a procedure, while remaining in a non-interfering location.

Manual entry capabilities may also be provided, such as through the use of a touch screen display 708. Alternately, other pointing devices (not shown), such as a mouse, trackball, or force post may be utilized, however it may be beneficial to minimize the necessity for a surgeon to remove his or her hands from the handles during a procedure. Finally, display commands may be received from a surgeon via the microphone in response to verbal commands. Alternately, an auxiliary display and input device may be provided to allow an assistant to the surgeon to be responsible for manual data entry during a procedure.

Figure 16:
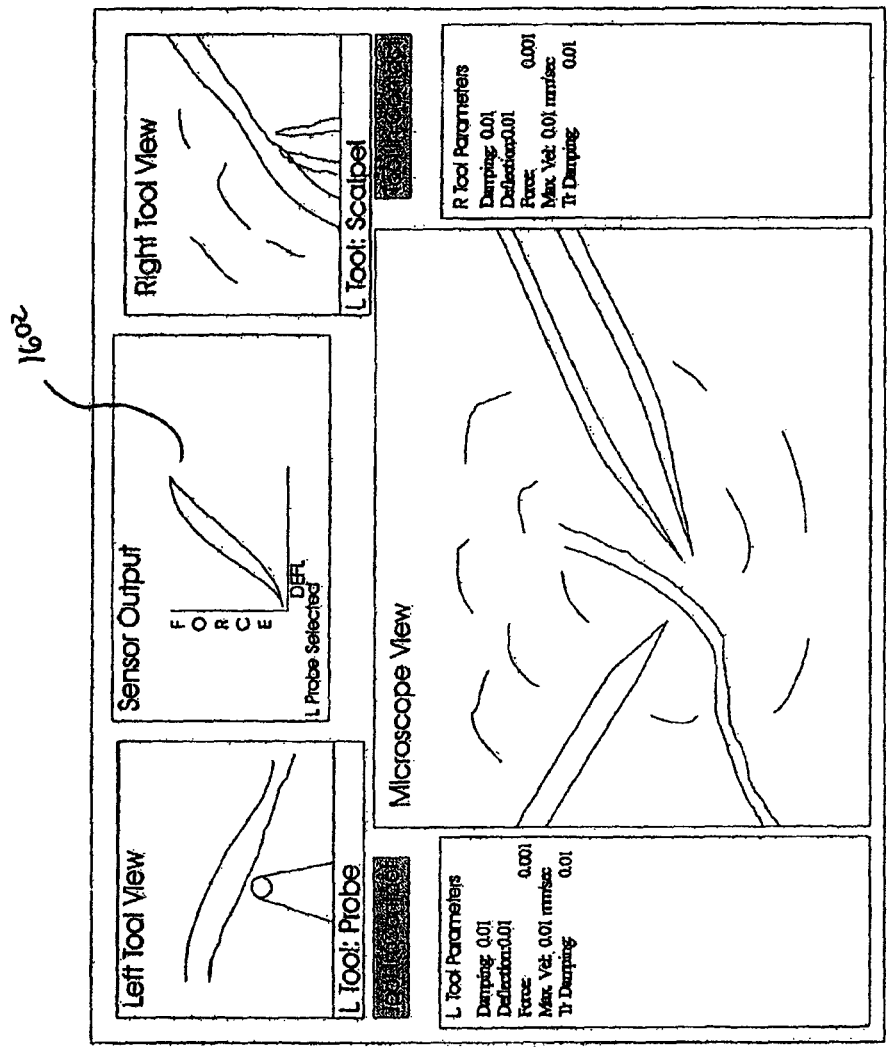
FIG. 16 shows a notional augmented microsurgical interface (hereafter "AMI") for a controller robot.

Instrument eye view displays may either be provided adjacent to the left and right robotic arms, where the surgeon is located immediately adjacent to the surgical field, or through instrument eye view displays 1604, 1606 incorporated into a display presentation on the workstation (such as is shown in FIG. 16). The use of a graphical user interface allows displays to be generated by the controller portion based on the needs of the surgeon at that point in a procedure, or in response to pre-programmed or manually selected parameters provide by the surgeon.

In addition to force and motion feedback provided to the surgeon through the handles, visual feedback can be provided through the display on the workstation. A notional display is shown in FIG. 16 showing an illustrative force/response curve resultant 1602 from pressing a probe as discussed above against tissue, showing both a force deflection curve 1608 resultant from imposing the probe against the tissue, as well as a hysteresis curve 1610 resultant from a controlled withdrawal of the probe from the contact with the tissue. Selection of sensor displays may be voice activated, such that a surgeon can reconfigure the display as required during a procedure. Alternately, the reconfiguring of the display can be the responsibility of an assistant in verbal communication with the surgeon during the procedure, such as through an auxiliary interface (shown in FIG. 8).

The controller portion 606 of the controller robot 10 may be able to cross control instruments when selected. Thus, the operator could elect to control a instrument on a left robotic arm through a right handle on the workstation. The controller logic may provide additional functionality during such cross-control utilization, such as locking out the non-used control to limit the likelihood of control confusion resulting from simultaneously cross controlling multiple instruments. Additionally, display parameters may be imposed during such cross-controlled utilization, such as enforcing the selected instrument's instrument-eye view for the primary display during cross-controlled utilization.

The controller portion 606 of the controller robot 10 may include a general purpose computer operating a program for controlling motion of the robotic arms as a result of input from a surgeon via the workstation. Accordingly, the controller software may be designed to enable to controller to assist the surgeon in varying ways, such as the imposed limitations associated with cross-controlling discussed above, or the generation of the force/response and hysteresis display shown in FIG. 16

Figure 8:
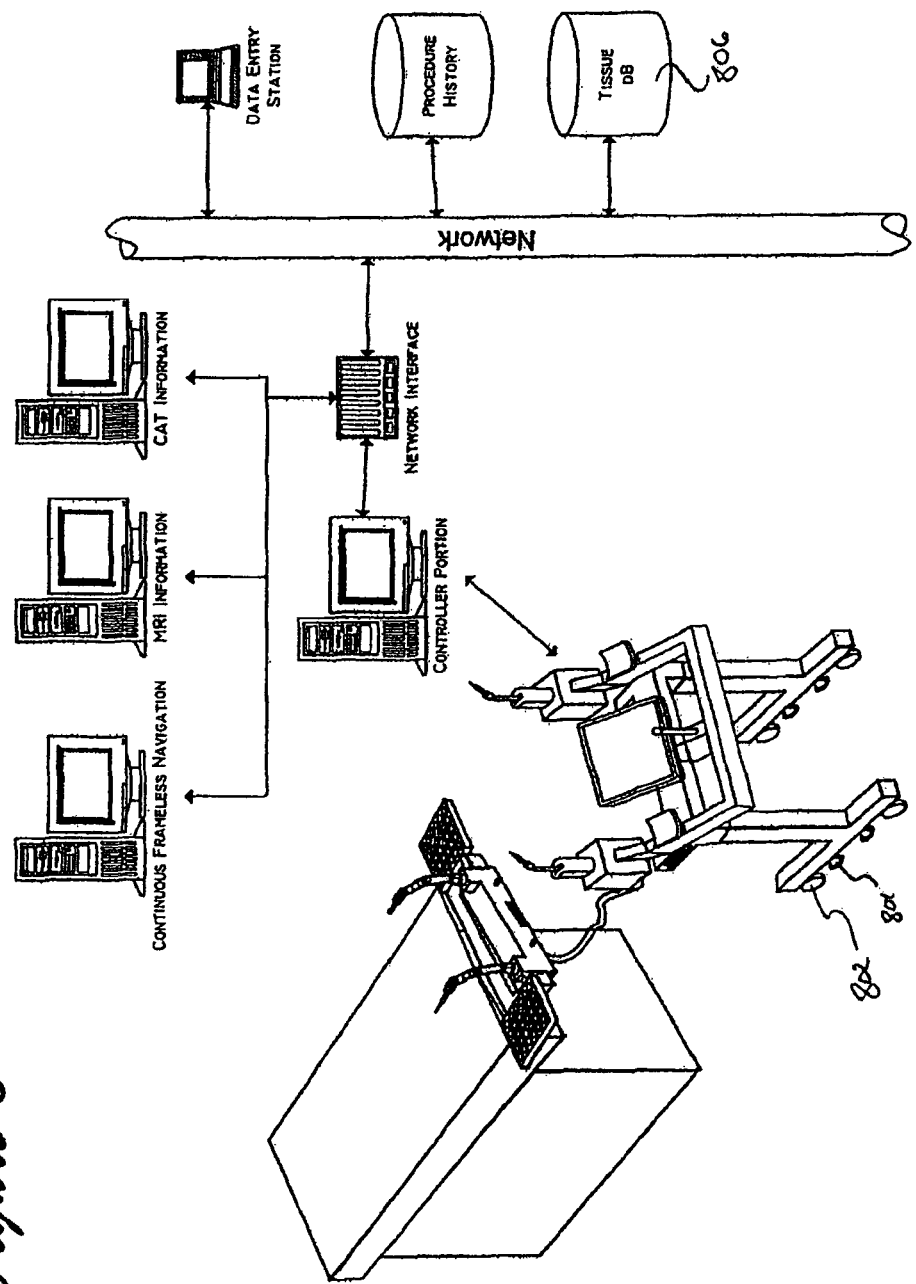
FIG. 8 shows a controller robot in an operating room environment.

The information obtained from a sensor such as the probe illustrated in FIG. 12 may be used for more than simple feedback to the surgeon. Analytical methods may be applied to the results to provide characterizations to a surgeon. For example, tissue stiffness or hysteresis values obtained from force/position information obtained from a probe may be compared to cataloged tissue characteristic inform such as information stored in a remote database 806 as shown in FIG. 8. The characteristics of the tissue may be matched with known tissue values, or may be compared with known values for particular tissue type selected by the surgeon. Other sensors may be selected as useful during the procedure (while such sensors are incorporated into a instrument unit or magazine) to allow a surgeon to obtain a variety of parameters (temperature, mechanical characteristics of tissue, oxygen saturation of blood adjacent to a surgical site, etc.), or to allow the surgeon to select control points in a surgical field. Such control points may be utilized to identify boundaries for allowable motion of the instruments or other elements of the robotics portion of the controller robot. Furthermore, connections to external systems such as continuous frameless navigation capabilities may allow the externally obtained data to be superimposed into displays presented on the workstation, such as a microscope view The principal purpose of the controller portion, 606 however, is to translate the inputs of the surgeon as provided through the handles into motions made by instruments engaged to the arms of the robotics portion. Parameters may be provided by the surgeon to affect the motion of the robotic arms and instruments in response to input commands provided by a surgeon through the handles. As discussed above, scaling of motions and forces may assist a surgeon in working in miniature, as may be required during some procedures. Additionally, damping parameters may be applied to provide increased controllability of instruments during a procedure.

The use of parameters may be implemented to provide a robust situation for motion of the instruments, such that maximum speed constraints, maximum motion constraints, motion damping, and controlled area prohibitions may be implemented as requested by a surgeon to assist the surgeon during a procedure. Controlled area prohibitions may be implemented based on control points identified by the surgeon, such that the controller portion may maintain a spatial model of the geometry of the patient and surrounding structures to prevent contact between instruments or any other portion of the robotics portion and prescribed areas. Offsets may be provided based on control points, such that the actual geometry of a prescribed area may be determined based on located reference points without requiring contact with the actual prescribed area, or to impose a no-contact safety margin between a prescribed area and an instrument or other part of the robotics portion.

The inviolability of the prescribed area may further be enhanced through the implementation of predictive motion modeling to generate expected position information, such that interference determinations between a prescribed area and an instrument position may be based not only on the position of the instrument, but also on the existing path of the instrument in motion, such that potential or predicted contact with a prescribed region may be signaled to the surgeon prior to such contact occurring, as well as allowing smoothing of the motion of the instrument adjacent to such a prescribed area. For example, as the contact potential measured as a factor of distance, direction of travel, and instrument speed, increases, the controller portion 606 may automatically increase motion damping and decrease maximum instrument velocity allowable, to provide the surgeon with greater control adjacent to the prescribed portion.

The ability to impose motion constraints, such as maximum instrument velocity, maximum instrument acceleration, and maximum instrument force, may be implemented to limit the likelihood of unwanted contact or spurious motions by the instrument. Force limitations may be applied to prevent damage to tissue which could result from over-application of force to tissue. Accordingly, it may be beneficial to provide for rapid configuration of the instrument force limit, to allow a surgeon to vary the instrument force limit based on an expected tissue type. Such a determination may further be assisted through the use of a catalog of force limitations based on tissue type, such that tissue type determinations obtained through external analysis, such as magnetic resonance imaging or computer aided tomography, may be applied to the spatial model of the surgical field to vary force limits based on tissue types defined by the external analysis.

The controller portion may be provided with a means for communicating information obtained during a procedure with external processors, to allow integration of the information utilized by the controller portion with information in use by other equipment in the surgical theater or hospital environment in general. For example, a network connection may be utilized by the controller portion to receive data obtained by magnetic resonance imaging or computer aided tomography to provide information for a spatial model of the surgical field. Alternately, the positions of each portion of the robotic arms may be used to determine the position of an instrument, such that the information could be exported to continuous frameless navigation equipment to allow the position of the instrument within the surgical field to be communicated to and integrated with the spatial information contained within the continuous frameless navigation equipment, or within the imagery presented by a enhanced viewing equipment, such as a electronic microscope. Other information, such as control points, could also be communicated between the pieces of equipment, such that the information could be overlayed into the other pieces of equipment. For example, a pre-defined prescribed area could be shaded in an electronic presentation of a microscope or instrument eye view, to inform the surgeon of the presence of and location of the prescribed area during a procedure, without requiring the surgeon to change attention from one display to another.

The exporting of information from the controller portion to external equipment may also allow remote storage of historical procedure information, such as the instrument selection and instrument position at any point during a procedure, such that the stored information could be later used to replay a procedure for teaching or review purposes. Furthermore, since the connection between the surgeon and the robotics portion is electrical, the stored information could be utilized to generate a replay of the handle positions and feedbacks, to allow a physician to follow through the procedures without actually creating motion of a robotics portion, while viewing the displays presented to the surgeon during the procedure.

Stored data may also be utilized to generate predictive selection of instruments for a surgeon prior to and during a procedure. For example, a certain surgeon may utilize a specific group of instruments for a specific type of procedure, distinguishable from the instruments that a different surgeon would select. Archived instrument selection information would allow provisioning of instrument trays based on the surgeons prior instrument selections, reducing the effort required to determine instrument provisioning for a procedure. Alternately, expected instrument information could be presented to an assistant to the physician to allow the assistant to review and confirm instrument selection based on the expected instrument selections, such as through the auxiliary workstation, further improving the efficiency of instrument provisioning in the surgical theater.

Finally, archived instrument selection information could be used administratively, such as to generate billings for instruments used during a procedure. Such use would reduce the administrative overhead associated with determining instrument usage for billing after a procedure.

Other variations and modifications of the present invention will be apparent to those of skill in the art, and it is the intent of the appended claims that such variations and modifications be covered. The particular values and configurations discussed above can be varied and are cited merely to illustrate a particular embodiment of the present invention and are not intended to limit the scope of the invention. It is contemplated that the use of the present invention can involve components having different characteristics as long as the principles of the invention are followed.

What is claimed is:

1. A controller robot for performing surgical procedures, the controller comprising:
  a robotics portion, the robotics portion comprising an arm, a first instrument magazine attached to the arm, and a plurality of different surgical instruments in the first instrument magazine, wherein the first instrument magazine and the plurality of surgical instruments move together with the arm;
  a workstation portion, the workstation portion comprising a display and an input device;
  a controller portion, the controller portion comprising hardware and software for transforming input provided by a surgeon operator via an interface portion into motion of a selected one of the surgical instruments;
  an instrument tray holding a plurality of additional instrument magazines; and
  wherein the controller portion further comprises instructions that cause the robotics portion to exchange the first instrument magazine with one of the additional instrument magazines from the instrument tray.

2. The controller robot of claim 1, wherein said interface portion further comprises a microphone for receiving spoken input from a surgeon operator, and wherein said controller portion selects a surgical instrument unit for engagement to the robotics arm dependant on input received via the microphone.

3. The controller robot of claim 1, wherein the robotics portion further comprises a left robotics arm and a right robotics arm, the robotics arms adapted to alternately engage varying surgical instruments.

4. The controller robot of claim 3, where said robotics portion further comprises a left instrument magazine attached to the left arm and having a plurality of surgical instruments for the left arm and a right instrument magazine attached to the right arm and having a plurality of surgical instruments for the right arm, the surgical instruments of each instrument magazine being adapted to alternately engage the robotics arms.

5. The controller robot of claim 4, wherein the controller portion further comprises capability to direct the left and right robotics arms to select specific surgical instruments for engagement to the robotics arms.

6. The controller robot of claim 5, wherein the varying surgical instrument units are selected dependant on a procedure to be performed.

7. The controller robot of claim 6, wherein the surgical instruments making up the left instrument magazine are not identical to the varying surgical instruments making up the right instrument magazine.

8. A controller robot for performing surgical procedures, the controller comprising:
 a robotics portion, the robotics portion comprising an arm, a first surgical instrument unit having a plurality of different surgical instruments that move together with the arm;
 a workstation portion, the workstation portion comprising a display and an input device;
 a controller portion, the controller portion comprising hardware and software for transforming input provided by a surgeon operator via an interface portion into motion of a selected one of the surgical instruments;
 an instrument tray holding a plurality of additional surgical instrument units; and
 wherein the controller portion further comprises instructions that cause the robotics portion to exchange the first surgical instrument unit with one of the additional surgical instrument units from the instrument tray.

9. A robotic system for surgical procedures, comprising:
 a workstation having a dock configured to mate with an operating table such that the workstation is indexed to a known location relative to the table;
 a robotics portion comprising a handle configured to be grasped by an operator, an arm, and a first surgical instrument unit having a plurality of different surgical instruments that move together with the arm; and
 a controller operatively coupled to the handle and to the arm, wherein the controller is configured to transform input provided by the surgeon operator via the handle into motion of the surgical instrument unit;
 an instrument tray holding a plurality of additional surgical instrument units; and
 wherein the controller further comprises instructions that cause the robotics portion to exchange the first surgical instrument unit with one of the additional surgical instrument units from the instrument tray.

10. The robotic system of claim 9, wherein the robotic portion comprises a first handle and a second handle, a first arm associated with the first handle and a second arm associated with the second handle, the first surgical instrument unit has a first plurality of instruments configured to be carried by the first arm, and the system further comprises a second surgical instrument unit having a second plurality of instruments configured to be carried by the second arm.

11. The robotic system of claim 10 wherein the workstation further comprises rollers configured to transport the workstation.

12. The robotic system of claim 10 wherein the robotics portion further comprises an interchange block carried by the arm, and wherein the interchange block and the surgical instruments are configured so that the surgical instruments are interchangeably attachable to the interchange block.

13. The robotic system of claim 10 wherein the first surgical instrument unit further comprises a magazine and the plurality of surgical instruments are carried by the magazine.

14. The robotic system of claim 13 wherein the magazine comprises a tray proximate to the arm.

15. The robotic system of claim 14 wherein the magazine comprises a rotary instrument holder attached to the arm and configured to rotate about a longitudinal axis of the magazine.

* * * * *